(12) United States Patent
Mercanzini et al.

(10) Patent No.: US 11,738,192 B2
(45) Date of Patent: Aug. 29, 2023

(54) NEUROSTIMULATION DEVICE

(71) Applicant: Aleva Neurotherapeutics, Lausanne (CH)

(72) Inventors: André Mercanzini, Saint Sulpice (CH); Zbynek Struzka, Lausanne (CH); Jason Jinyu Ruan, Lausanne (CH); Pascal Harbi, Lausanne (CH); Alain Jordan, Lausanne (CH)

(73) Assignee: Aleva Neurotherapeutics

( * ) Notice: Subject to any disclaimer, the term of this patent is extended or adjusted under 35 U.S.C. 154(b) by 0 days.

(21) Appl. No.: 17/667,052

(22) Filed: Feb. 8, 2022

(65) Prior Publication Data

US 2022/0161024 A1 May 26, 2022

Related U.S. Application Data

(63) Continuation of application No. 16/901,583, filed on Jun. 15, 2020, now Pat. No. 11,266,830, which is a continuation of application No. 15/910,278, filed on Mar. 2, 2018, now Pat. No. 10,702,692.

(51) Int. Cl.
*A61N 1/05* (2006.01)
*A61N 1/36* (2006.01)
*A61B 90/00* (2016.01)

(52) U.S. Cl.
CPC ......... *A61N 1/0539* (2013.01); *A61N 1/0534* (2013.01); *A61N 1/0551* (2013.01); *A61N 1/3605* (2013.01); *A61B 2090/3966* (2016.02)

(58) Field of Classification Search
None
See application file for complete search history.

(56) References Cited

U.S. PATENT DOCUMENTS

| | | |
|---|---|---|
| 4,245,645 A | 1/1981 | Arseneault et al. |
| 4,550,733 A | 11/1985 | Liss et al. |
| 4,837,049 A | 6/1989 | Byers et al. |
| 4,917,093 A | 4/1990 | Dufresne et al. |
| 4,928,297 A | 5/1990 | Tsutsui et al. |
| 4,969,468 A | 11/1990 | Byers et al. |
| 4,989,617 A | 2/1991 | Memberg et al. |
| 5,095,905 A | 3/1992 | Klepinski |
| 5,215,088 A | 6/1993 | Normann et al. |
| 5,237,996 A | 8/1993 | Waldman et al. |
| 5,345,936 A | 9/1994 | Pomeranz et al. |
| 5,391,250 A | 2/1995 | Cheney et al. |

(Continued)

FOREIGN PATENT DOCUMENTS

| | | |
|---|---|---|
| CN | 1261801 A | 8/2000 |
| CN | 101027085 A | 8/2007 |

(Continued)

OTHER PUBLICATIONS

US 8,388,533 B2, 03/2013, Hafezi et al. (withdrawn)

(Continued)

*Primary Examiner* — Paula J Stice
(74) *Attorney, Agent, or Firm* — Foley & Lardner LLP

(57) ABSTRACT

The present disclosure describes an implantable lead device that includes an internal support comb. The support comb can include one or more faces that enable the alignment, routing, and holding of the lead device's internal wires. The support comb can enable the interconnection of the wires with to the microelectrode film that includes the lead device's electrodes.

20 Claims, 22 Drawing Sheets

(56) References Cited

U.S. PATENT DOCUMENTS

| | | |
|---|---|---|
| 5,400,784 A | 3/1995 | Durand et al. |
| 5,419,777 A | 5/1995 | Hofling |
| 5,458,629 A | 10/1995 | Baudino et al. |
| 5,496,369 A | 3/1996 | Howard, III |
| 5,524,338 A | 6/1996 | Martyniuk et al. |
| 5,628,317 A | 5/1997 | Starkebaum et al. |
| 5,643,330 A | 7/1997 | Holsheimer et al. |
| 5,679,355 A | 10/1997 | Alexander et al. |
| 5,683,422 A | 11/1997 | Rise |
| 5,697,651 A | 12/1997 | Fernandes |
| 5,697,975 A | 12/1997 | Howard et al. |
| 5,702,429 A | 12/1997 | King |
| 5,713,922 A | 2/1998 | King |
| 5,713,923 A | 2/1998 | Ward et al. |
| 5,716,377 A | 2/1998 | Rise et al. |
| 5,727,552 A | 3/1998 | Ryan |
| 5,752,979 A | 5/1998 | Benabid |
| 5,755,759 A | 5/1998 | Cogan |
| 5,782,798 A | 7/1998 | Rise |
| 5,797,970 A | 8/1998 | Pouvreau |
| 5,800,474 A | 9/1998 | Benabid et al. |
| 5,800,535 A | 9/1998 | Howard, III |
| 5,814,092 A | 9/1998 | King |
| 5,824,029 A | 10/1998 | Weijand et al. |
| 5,792,186 A | 11/1998 | Rise |
| 5,833,709 A | 11/1998 | Rise et al. |
| 5,833,714 A | 11/1998 | Loeb |
| 5,843,148 A | 12/1998 | Gijsbers et al. |
| 5,893,883 A | 4/1999 | Torgerson et al. |
| 5,913,882 A | 6/1999 | King |
| 5,921,924 A | 7/1999 | Avitall |
| 5,927,277 A | 7/1999 | Baudino et al. |
| 5,941,906 A | 8/1999 | Barreras et al. |
| 5,957,958 A | 9/1999 | Schulman et al. |
| 5,975,085 A | 11/1999 | Rise |
| 5,978,702 A | 11/1999 | Ward et al. |
| 5,991,668 A | 11/1999 | Leinders et al. |
| 6,011,996 A | 1/2000 | Gielen et al. |
| 6,018,682 A | 1/2000 | Rise |
| 6,024,095 A | 2/2000 | Stanley, III |
| 6,033,403 A | 3/2000 | Tu et al. |
| 6,038,480 A | 3/2000 | Hrdlicka et al. |
| 6,050,992 A | 4/2000 | Nichols |
| 6,094,598 A | 7/2000 | Elsberry et al. |
| 6,104,960 A | 8/2000 | Duysens et al. |
| 6,109,269 A | 8/2000 | Rise et al. |
| 6,125,300 A | 9/2000 | Weijand et al. |
| 6,128,537 A | 10/2000 | Rise |
| 6,129,685 A | 10/2000 | Howard, III |
| 6,161,047 A | 12/2000 | King et al. |
| 6,205,359 B1 | 3/2001 | Boveja |
| 6,205,361 B1 | 3/2001 | Kuzma et al. |
| 6,216,043 B1 | 4/2001 | Swanson et al. |
| 6,227,203 B1 | 5/2001 | Rise et al. |
| 6,253,109 B1 | 6/2001 | Gielen |
| 6,253,110 B1 | 6/2001 | Brabec et al. |
| 6,263,237 B1 | 7/2001 | Rise |
| 6,266,564 B1 | 7/2001 | Hill et al. |
| 6,295,476 B1 | 9/2001 | Schaenzer |
| 6,301,492 B1 | 10/2001 | Zonenshayn |
| 6,319,241 B1 | 11/2001 | King et al. |
| 6,330,466 B1 | 12/2001 | Hofmann et al. |
| 6,337,997 B1 | 1/2002 | Rise |
| 6,343,226 B1 | 1/2002 | Sunde et al. |
| 6,353,762 B1 | 3/2002 | Baudino et al. |
| 6,356,784 B1 | 3/2002 | Lozano et al. |
| 6,356,786 B1 | 3/2002 | Rezai et al. |
| 6,356,787 B1 | 3/2002 | Rezai et al. |
| 6,364,875 B1 | 4/2002 | Stanley, III |
| 6,366,813 B1 | 4/2002 | DiLorenzo |
| 6,374,140 B1 | 4/2002 | Rise |
| 6,375,666 B1 | 4/2002 | Mische |
| 6,379,353 B1 | 4/2002 | Nichols |
| 6,415,187 B1 | 7/2002 | Kuzma et al. |
| 6,434,431 B1 | 8/2002 | Camps et al. |
| 6,459,936 B2 | 10/2002 | Fischell et al. |
| 6,479,999 B1 | 11/2002 | Demeester et al. |
| 6,484,059 B2 | 11/2002 | Gielen |
| 6,493,590 B1 | 12/2002 | Wessman et al. |
| 6,510,347 B2 | 1/2003 | Borkan |
| 6,529,774 B1 | 3/2003 | Greene |
| 6,538,443 B2 | 3/2003 | Morich et al. |
| 6,549,812 B1 | 4/2003 | Smits |
| 6,556,873 B1 | 4/2003 | Smits |
| 6,560,472 B2 | 5/2003 | Hill et al. |
| 6,560,486 B1 | 5/2003 | Osorio et al. |
| 6,581,046 B1 | 6/2003 | Ahissar |
| 6,587,733 B1 | 7/2003 | Cross et al. |
| 6,591,128 B1 | 7/2003 | Wu et al. |
| 6,594,524 B2 | 7/2003 | Esteller et al. |
| 6,597,953 B2 | 7/2003 | Boling |
| 6,643,552 B2 | 11/2003 | Edell et al. |
| 6,671,544 B2 | 12/2003 | Baudino |
| 6,675,046 B2 | 1/2004 | Holsheimer |
| 6,687,538 B1 | 2/2004 | Hrdlicka et al. |
| 6,690,973 B2 | 2/2004 | Hill et al. |
| 6,708,064 B2 | 3/2004 | Rezai |
| 6,718,208 B2 | 4/2004 | Hill et al. |
| 6,718,211 B2 | 4/2004 | Smits |
| 6,741,893 B2 | 5/2004 | Smits |
| 6,745,079 B2 | 6/2004 | King |
| 6,757,970 B1 | 7/2004 | Kuzma et al. |
| 6,795,737 B2 | 9/2004 | Gielen et al. |
| 6,804,552 B2 | 10/2004 | Thompson et al. |
| 6,818,396 B1 | 11/2004 | Bloch et al. |
| 6,829,498 B2 | 12/2004 | Kipke et al. |
| 6,850,802 B2 | 2/2005 | Holsheimer |
| 6,871,098 B2 | 3/2005 | Nuttin et al. |
| 6,882,881 B1 | 4/2005 | Lesser et al. |
| 6,892,097 B2 | 5/2005 | Holsheimer |
| 6,892,438 B1 | 5/2005 | Hill et al. |
| 6,904,306 B1 | 6/2005 | Wu et al. |
| 6,909,920 B2 | 6/2005 | Lokhoff et al. |
| 6,920,359 B2 | 7/2005 | Meadows et al. |
| 6,928,320 B2 | 8/2005 | King |
| 6,950,706 B2 | 9/2005 | Rodriguez et al. |
| 6,950,709 B2 | 9/2005 | Baudino |
| 6,978,171 B2 | 12/2005 | Goetz et al. |
| 6,978,178 B2 | 12/2005 | Sommer et al. |
| 6,999,819 B2 | 2/2006 | Swoyer et al. |
| 7,006,859 B1 | 2/2006 | Osorio et al. |
| 7,010,351 B2 | 3/2006 | Firlik et al. |
| 7,010,356 B2 | 3/2006 | Jog et al. |
| 7,024,246 B2 | 4/2006 | Acosta et al. |
| 7,035,690 B2 | 4/2006 | Goetz |
| 7,047,082 B1 | 5/2006 | Schrom et al. |
| 7,047,084 B2 | 5/2006 | Erickson et al. |
| 7,050,856 B2 | 5/2006 | Stypulkowski |
| 7,051,419 B2 | 5/2006 | Schrom et al. |
| 7,061,240 B2 | 6/2006 | Ham et al. |
| 7,063,767 B1 | 6/2006 | Tyson et al. |
| 7,076,292 B2 | 7/2006 | Forsberg |
| 7,077,822 B1 | 7/2006 | Howard, III |
| 7,107,104 B2 | 9/2006 | Keravel et al. |
| 7,133,718 B2 | 11/2006 | Bakken et al. |
| 7,146,222 B2 | 12/2006 | Boling |
| 7,151,961 B1 | 12/2006 | Whitehurst et al. |
| 7,174,219 B2 | 2/2007 | Wahlstrand et al. |
| 7,177,701 B1 | 2/2007 | Pianca |
| 7,181,288 B1 | 2/2007 | Rezai et al. |
| 7,184,829 B2 | 2/2007 | Hill et al. |
| 7,187,978 B2 | 3/2007 | Malek et al. |
| 7,191,016 B2 | 3/2007 | Marshall et al. |
| 7,191,018 B2 | 3/2007 | Gielen et al. |
| 7,198,626 B2 | 4/2007 | Lee et al. |
| 7,200,439 B2 | 4/2007 | Zdeblick et al. |
| 7,203,548 B2 | 4/2007 | Whitehurst et al. |
| 7,204,798 B2 | 4/2007 | Zdeblick et al. |
| 7,204,833 B1 | 4/2007 | Osorio et al. |
| 7,209,787 B2 | 4/2007 | DiLorenzo |
| 7,212,851 B2 | 5/2007 | Donoghue et al. |
| 7,212,867 B2 | 5/2007 | Van Venroo et al. |
| 7,214,189 B2 | 5/2007 | Zdeblick |
| 7,216,000 B2 | 5/2007 | Sieracki et al. |

(56) References Cited

U.S. PATENT DOCUMENTS

| | | |
|---|---|---|
| 7,216,001 B2 | 5/2007 | Hacker et al. |
| 7,231,256 B2 | 6/2007 | Wahlstrand et al. |
| 7,236,822 B2 | 6/2007 | Dobak, III |
| 7,242,984 B2 | 7/2007 | DiLorenzo |
| 7,276,061 B2 | 10/2007 | Schaer et al. |
| 7,280,867 B2 | 10/2007 | Frei et al. |
| 7,282,030 B2 | 10/2007 | Frei et al. |
| 7,282,050 B2 | 10/2007 | Starkebaum et al. |
| 7,286,878 B2 | 10/2007 | Stypulkowski |
| 7,286,882 B2 | 10/2007 | Cole |
| 7,288,066 B2 | 10/2007 | Drew |
| 7,289,851 B2 | 10/2007 | Gunderson et al. |
| 7,289,852 B2 | 10/2007 | Helfinstine et al. |
| 7,295,880 B2 | 11/2007 | Gielen |
| 7,298,143 B2 | 11/2007 | Jaermann et al. |
| 7,307,223 B2 | 12/2007 | Tyson et al. |
| 7,313,430 B2 | 12/2007 | Urquhart et al. |
| 7,313,440 B2 | 12/2007 | Miesel |
| 7,315,759 B2 | 1/2008 | Markowitz et al. |
| 7,317,947 B2 | 1/2008 | Wahlstrand et al. |
| 7,317,948 B1 | 1/2008 | King et al. |
| 7,319,899 B2 | 1/2008 | Keizer |
| 7,319,904 B2 | 1/2008 | Cross et al. |
| 7,321,798 B2 | 1/2008 | Muhlenberg et al. |
| 7,321,837 B2 | 1/2008 | Osorio et al. |
| 7,322,832 B2 | 1/2008 | Kronich et al. |
| 7,328,057 B2 | 2/2008 | Freas et al. |
| 7,328,068 B2 | 2/2008 | Spinelli et al. |
| 7,328,069 B2 | 2/2008 | Gerber |
| 7,330,760 B2 | 2/2008 | Heruth et al. |
| 7,337,010 B2 | 2/2008 | Howard et al. |
| 7,343,206 B2 | 3/2008 | Sage et al. |
| 7,346,395 B2 | 3/2008 | Lozano et al. |
| 7,356,369 B2 | 4/2008 | Phillips et al. |
| 7,359,837 B2 | 4/2008 | Drew |
| 7,366,572 B2 | 4/2008 | Heruth et al. |
| 7,367,956 B2 | 5/2008 | King |
| 7,369,891 B2 | 5/2008 | Augustijn et al. |
| 7,369,893 B2 | 5/2008 | Gunderson |
| 7,369,894 B2 | 5/2008 | Gerber |
| 7,385,443 B1 | 6/2008 | Denison |
| 7,388,378 B2 | 6/2008 | Gray et al. |
| 7,389,147 B2 | 6/2008 | Wahlstrand et al. |
| 7,390,311 B2 | 6/2008 | Hildebrand et al. |
| 7,391,257 B1 | 6/2008 | Denison et al. |
| 7,392,089 B2 | 6/2008 | Wahlstrand et al. |
| 7,395,113 B2 | 7/2008 | Heruth et al. |
| 7,400,927 B1 | 7/2008 | Litvin |
| 7,403,820 B2 | 7/2008 | DiLorenzo |
| 7,406,351 B2 | 7/2008 | Wesselink |
| 7,418,292 B2 | 8/2008 | Shafer |
| 7,421,297 B2 | 9/2008 | Giftakis et al. |
| 7,427,280 B2 | 9/2008 | Gerber |
| 7,429,938 B1 | 9/2008 | Corndorf |
| 7,433,734 B2 | 10/2008 | King |
| 7,442,183 B2 | 10/2008 | Baudino et al. |
| 7,447,545 B2 | 11/2008 | Heruth et al. |
| 7,450,996 B2 | 11/2008 | MacDonald et al. |
| 7,463,917 B2 | 12/2008 | Martinez |
| 7,463,928 B2 | 12/2008 | Lee et al. |
| 7,474,247 B1 | 1/2009 | Heinks et al. |
| 7,479,910 B1 | 1/2009 | Heinks et al. |
| 7,483,748 B2 | 1/2009 | Torgerson et al. |
| 7,489,966 B2 | 2/2009 | Leinders et al. |
| 7,489,970 B2 | 2/2009 | Lee et al. |
| 7,491,181 B2 | 2/2009 | Heruth et al. |
| 7,497,844 B2 | 3/2009 | Spear et al. |
| 7,497,863 B2 | 3/2009 | Solar et al. |
| 7,502,217 B2 | 3/2009 | Zhao et al. |
| 7,505,815 B2 | 3/2009 | Lee et al. |
| 7,505,869 B2 | 3/2009 | Hartlaub |
| 7,515,961 B2 | 4/2009 | Germanson et al. |
| 7,519,431 B2 | 4/2009 | Goetz et al. |
| 7,519,432 B2 | 4/2009 | Bolea et al. |
| 7,520,890 B2 | 4/2009 | Phillips |
| 7,526,339 B2 | 4/2009 | Lahti et al. |
| 7,526,340 B2 | 4/2009 | Drew |
| 7,526,341 B2 | 4/2009 | Goetz et al. |
| 7,529,582 B1 | 5/2009 | DiLorenzo |
| 7,529,586 B2 | 5/2009 | Wahlstrand et al. |
| 7,542,803 B2 | 6/2009 | Heruth et al. |
| 7,546,164 B2 | 6/2009 | King |
| 7,546,166 B2 | 6/2009 | Michels et al. |
| 7,548,775 B2 | 6/2009 | Kipke et al. |
| 7,548,786 B2 | 6/2009 | Lee et al. |
| 7,551,951 B1 | 6/2009 | Osorio et al. |
| 7,551,960 B2 | 6/2009 | Forsberg et al. |
| 7,555,345 B2 | 6/2009 | Wahlstrand et al. |
| 7,561,921 B2 | 7/2009 | Phillips et al. |
| 7,563,141 B2 | 7/2009 | Alexander et al. |
| 7,563,541 B2 | 7/2009 | Howard et al. |
| 7,578,819 B2 | 8/2009 | Bleich et al. |
| 7,580,756 B2 | 8/2009 | Schulte et al. |
| 7,582,387 B2 | 9/2009 | Howard et al. |
| 7,590,451 B2 | 9/2009 | Tronnes et al. |
| 7,590,453 B2 | 9/2009 | Heruth et al. |
| 7,590,455 B2 | 9/2009 | Heruth et al. |
| 7,591,970 B2 | 9/2009 | Olson |
| 7,594,828 B2 | 9/2009 | Alexander et al. |
| 7,594,889 B2 | 9/2009 | St. Ores et al. |
| 7,596,399 B2 | 9/2009 | Singhal et al. |
| 7,596,408 B2 | 9/2009 | Singhal et al. |
| 7,596,415 B2 | 9/2009 | Brabec et al. |
| 7,599,730 B2 | 10/2009 | Hunter et al. |
| 7,603,161 B2 | 10/2009 | Wurmfeld et al. |
| 7,603,177 B2 | 10/2009 | Sieracki et al. |
| 7,604,629 B2 | 10/2009 | Gerber et al. |
| 7,604,644 B2 | 10/2009 | Schulte et al. |
| 7,608,458 B2 | 10/2009 | Soykan et al. |
| 7,610,083 B2 | 10/2009 | Drew et al. |
| 7,611,483 B2 | 11/2009 | Gerber et al. |
| 7,614,743 B2 | 11/2009 | Geiger |
| 7,615,015 B2 | 11/2009 | Coleman |
| 7,616,998 B2 | 11/2009 | Nuttin et al. |
| 7,617,002 B2 | 11/2009 | Goetz |
| 7,620,454 B2 | 11/2009 | Dinsmoor et al. |
| 7,622,303 B2 | 11/2009 | Soykan et al. |
| 7,622,988 B2 | 11/2009 | Denison et al. |
| 7,623,053 B2 | 11/2009 | Terry et al. |
| 7,623,918 B2 | 11/2009 | Goetz |
| 7,623,919 B2 | 11/2009 | Goetz et al. |
| 7,623,923 B2 | 11/2009 | Gerber et al. |
| 7,623,930 B2 | 11/2009 | Zeijlemaker et al. |
| 7,624,293 B2 | 11/2009 | Osorio et al. |
| 7,628,780 B2 | 12/2009 | Bonner et al. |
| 7,631,415 B2 | 12/2009 | Phillips et al. |
| 7,632,225 B2 | 12/2009 | Stypulkowski |
| 7,635,541 B2 | 12/2009 | Scott et al. |
| 7,637,867 B2 | 12/2009 | Zdeblick |
| 7,640,059 B2 | 12/2009 | Forsberg et al. |
| 7,640,060 B2 | 12/2009 | Zdeblick |
| 7,641,992 B2 | 1/2010 | Howard et al. |
| 7,642,013 B2 | 1/2010 | Howard et al. |
| 7,647,111 B2 | 1/2010 | Ries et al. |
| 7,647,116 B2 | 1/2010 | Bauhahn |
| 7,647,117 B2 | 1/2010 | Bauhahn |
| 7,647,121 B2 | 1/2010 | Wahlstrand et al. |
| 7,650,291 B2 | 1/2010 | Rosenfeld et al. |
| 7,653,433 B2 | 1/2010 | Lozano et al. |
| 7,657,318 B2 | 2/2010 | King et al. |
| 7,657,319 B2 | 2/2010 | Goetz et al. |
| 7,660,620 B2 | 2/2010 | Zeijlemaker et al. |
| 7,660,630 B2 | 2/2010 | Dudding et al. |
| 7,662,140 B2 | 2/2010 | Heruth et al. |
| 7,662,509 B2 | 2/2010 | Howard et al. |
| 7,663,066 B2 | 2/2010 | Tyson et al. |
| 7,664,551 B2 | 2/2010 | Cigaina |
| 7,664,552 B2 | 2/2010 | Wahlstrand et al. |
| 7,668,601 B2 | 2/2010 | Hegland et al. |
| 7,671,594 B2 | 3/2010 | Gray |
| 7,676,271 B2 | 3/2010 | Wahlstrand et al. |
| 7,676,273 B2 | 3/2010 | Goetz et al. |
| 7,676,274 B2 | 3/2010 | Hung et al. |
| 7,680,540 B2 | 3/2010 | Jensen et al. |

(56) References Cited

U.S. PATENT DOCUMENTS

| | | | |
|---|---|---|---|
| 7,682,355 | B2 | 3/2010 | Gerber et al. |
| 7,682,745 | B2 | 3/2010 | Howard et al. |
| 7,684,860 | B2 | 3/2010 | Wahlstrand et al. |
| 7,684,866 | B2 | 3/2010 | Fowler et al. |
| 7,684,873 | B2 | 3/2010 | Gerber |
| 7,689,289 | B2 | 3/2010 | King |
| 7,697,972 | B2 | 4/2010 | Verard et al. |
| 7,697,995 | B2 | 4/2010 | Cross et al. |
| 7,706,124 | B2 | 4/2010 | Zhao et al. |
| 7,706,889 | B2 | 4/2010 | Gerber et al. |
| 7,711,421 | B2 | 5/2010 | Shafer et al. |
| 7,711,428 | B2 | 5/2010 | Janzig et al. |
| 7,711,436 | B2 | 5/2010 | Stone |
| 7,713,194 | B2 | 5/2010 | Zdeblick |
| 7,713,195 | B2 | 5/2010 | Zdeblick |
| 7,720,548 | B2 | 5/2010 | King |
| 7,729,768 | B2 | 6/2010 | White et al. |
| 7,729,780 | B2 | 6/2010 | Vardiman |
| 7,738,958 | B2 | 6/2010 | Zdeblick et al. |
| 7,742,823 | B2 | 6/2010 | King et al. |
| 7,756,588 | B2 | 7/2010 | Jog et al. |
| 7,765,012 | B2 | 7/2010 | Gerber |
| 7,769,472 | B2 | 8/2010 | Gerber |
| 7,797,029 | B2 | 9/2010 | Gibson et al. |
| 7,822,482 | B2 | 10/2010 | Gerber |
| 7,822,483 | B2 | 10/2010 | Stone et al. |
| 7,853,303 | B2 | 12/2010 | Nikumb et al. |
| 7,877,149 | B2 | 1/2011 | Zdeblick |
| 7,899,539 | B2 | 3/2011 | Whitehurst et al. |
| 7,925,329 | B2 | 4/2011 | Zdeblick et al. |
| 7,930,035 | B2 | 4/2011 | DiLorenzo |
| 7,935,056 | B2 | 5/2011 | Zdeblick |
| 7,941,202 | B2 | 5/2011 | Hetke et al. |
| 7,945,329 | B2 | 5/2011 | Bedenbaugh |
| 7,969,161 | B2 | 6/2011 | Behzadi et al. |
| 7,974,705 | B2 | 7/2011 | Zdeblick et al. |
| 7,978,064 | B2 | 7/2011 | Zdeblick et al. |
| 7,979,105 | B2 | 7/2011 | Kipke et al. |
| 7,983,751 | B2 | 7/2011 | Zdeblick et al. |
| 7,991,481 | B2 | 8/2011 | Benabid et al. |
| 8,000,794 | B2 | 8/2011 | Lozano |
| 8,000,808 | B2 | 8/2011 | Hegland et al. |
| 8,010,202 | B2 | 8/2011 | Shah et al. |
| 8,024,022 | B2 | 9/2011 | Schulman et al. |
| 8,032,224 | B2 | 10/2011 | Miesel et al. |
| 8,036,737 | B2 | 10/2011 | Goetz et al. |
| 8,036,743 | B2 | 10/2011 | Savage et al. |
| 8,036,748 | B2 | 10/2011 | Zdeblick et al. |
| 8,055,334 | B2 | 11/2011 | Savage et al. |
| 8,055,353 | B2 | 11/2011 | Kreidler et al. |
| 8,090,450 | B2 | 1/2012 | Swoyer et al. |
| 8,099,170 | B2 | 1/2012 | Jensen et al. |
| 8,108,049 | B2 | 1/2012 | King |
| 8,114,021 | B2 | 2/2012 | Robertson et al. |
| 8,115,618 | B2 | 2/2012 | Robertson et al. |
| 8,116,882 | B2 | 2/2012 | Kowalczewski |
| 8,121,687 | B2 | 2/2012 | Jensen et al. |
| 8,121,702 | B2 | 2/2012 | King |
| 8,123,684 | B2 | 2/2012 | Zdeblick |
| 8,170,676 | B2 | 5/2012 | Greenberg et al. |
| 8,171,621 | B2 | 5/2012 | Swanson et al. |
| 8,172,762 | B2 | 5/2012 | Robertson |
| 8,187,161 | B2 | 5/2012 | Li et al. |
| 8,195,308 | B2 | 6/2012 | Frank et al. |
| 8,204,586 | B2 | 6/2012 | Zdeblick |
| 8,224,417 | B2 | 7/2012 | Vetter |
| 8,224,462 | B2 | 7/2012 | Westlund et al. |
| 8,244,377 | B1 | 8/2012 | Pianca et al. |
| 8,258,962 | B2 | 9/2012 | Robertson et al. |
| 8,261,428 | B2 | 9/2012 | Fang et al. |
| 8,271,094 | B1 | 9/2012 | Moffitt et al. |
| 8,280,514 | B2 | 10/2012 | Lozano et al. |
| 8,295,943 | B2 | 10/2012 | Eggen et al. |
| 8,315,686 | B2 | 11/2012 | Llinas et al. |
| 8,321,025 | B2 | 11/2012 | Bedenbaugh |
| 8,332,020 | B2 | 12/2012 | Zdeblick |
| 8,332,046 | B2 | 12/2012 | Anderson et al. |
| 8,355,768 | B2 | 1/2013 | Masmanidis et al. |
| 8,374,703 | B2 | 2/2013 | Imran |
| 8,412,347 | B2 | 4/2013 | Zdeblick |
| 8,463,353 | B2 | 6/2013 | Seymour |
| 8,463,398 | B2 | 6/2013 | Jackson et al. |
| 8,467,877 | B2 | 6/2013 | Imran |
| 8,473,061 | B2 | 6/2013 | Moffitt et al. |
| 8,473,069 | B2 | 6/2013 | Bi et al. |
| 8,489,203 | B2 | 7/2013 | Ortmann |
| 8,509,872 | B2 | 8/2013 | Lee et al. |
| 8,509,876 | B2 | 8/2013 | Karmarkar |
| 8,509,920 | B2 | 8/2013 | Wahlstrand et al. |
| 8,560,085 | B2 | 10/2013 | Moffitt et al. |
| 8,565,894 | B2 | 10/2013 | Vetter et al. |
| 8,571,665 | B2 | 10/2013 | Moffitt et al. |
| 8,583,253 | B1 | 11/2013 | Shi et al. |
| 8,620,452 | B2 | 12/2013 | King et al. |
| 8,626,312 | B2 | 1/2014 | King et al. |
| 8,634,934 | B2 | 1/2014 | Kokones et al. |
| 8,644,903 | B1 | 2/2014 | Osa et al. |
| 8,649,879 | B2 | 2/2014 | Digiore et al. |
| 8,666,509 | B2 | 3/2014 | Howard et al. |
| 8,694,105 | B2 | 4/2014 | Martens et al. |
| 8,694,123 | B2 | 4/2014 | Wahlstrand et al. |
| 8,694,127 | B2 | 4/2014 | Pianca et al. |
| 8,731,673 | B2 | 5/2014 | Vetter et al. |
| 8,738,154 | B2 | 5/2014 | Zdeblick et al. |
| 8,744,596 | B2 | 6/2014 | Howard |
| 8,755,906 | B2 | 6/2014 | Moffitt et al. |
| 8,762,065 | B2 | 6/2014 | DiLorenzo |
| 8,774,891 | B1 | 7/2014 | Osa et al. |
| 8,788,056 | B2 | 7/2014 | King et al. |
| 8,788,063 | B2 | 7/2014 | Chen |
| 8,788,064 | B2 | 7/2014 | Mercanzini et al. |
| 8,792,993 | B2 | 7/2014 | Pianca et al. |
| 8,800,140 | B2 | 8/2014 | Hetke et al. |
| 8,825,175 | B2 | 9/2014 | King |
| 8,831,739 | B2 | 9/2014 | McCreery et al. |
| 8,831,742 | B2 | 9/2014 | Pianca et al. |
| 8,849,369 | B2 | 9/2014 | Cogan et al. |
| 8,849,415 | B2 | 9/2014 | Bedenbaugh |
| 8,862,242 | B2 | 10/2014 | Pianca |
| 8,874,232 | B2 | 10/2014 | Chen |
| 8,875,391 | B2 | 11/2014 | Pianca et al. |
| 8,897,891 | B2 | 11/2014 | Romero |
| 8,923,982 | B2 | 12/2014 | Howard |
| 8,934,965 | B2 | 1/2015 | Rogers et al. |
| 8,934,980 | B2 | 1/2015 | Pless et al. |
| 8,938,300 | B2 | 1/2015 | Rosero |
| 8,938,308 | B2 | 1/2015 | Meadows |
| 8,958,862 | B2 | 2/2015 | Hetke et al. |
| 8,968,331 | B1 | 3/2015 | Sochor |
| 8,977,335 | B2 | 3/2015 | Putz |
| 8,977,367 | B2 | 3/2015 | Elahi et al. |
| 8,989,864 | B2 | 3/2015 | Funderburk et al. |
| 9,008,747 | B2 | 4/2015 | Seymour et al. |
| 9,014,796 | B2 | 4/2015 | Kipke et al. |
| 9,044,590 | B2 | 6/2015 | Greenberg et al. |
| 9,061,134 | B2 | 6/2015 | Askin et al. |
| 9,079,013 | B2 | 7/2015 | Digiore et al. |
| 9,089,689 | B2 | 7/2015 | Govea |
| 9,089,690 | B2 | 7/2015 | Greenberg et al. |
| 9,095,267 | B2 | 8/2015 | Halpern et al. |
| 9,149,630 | B2 | 10/2015 | Howard et al. |
| 9,211,401 | B2 | 12/2015 | Frewin et al. |
| 9,211,402 | B2 | 12/2015 | Moffitt et al. |
| 9,220,897 | B2 | 12/2015 | Perryman et al. |
| 9,227,050 | B2 | 1/2016 | Romero |
| 9,248,272 | B2 | 2/2016 | Romero |
| 9,248,275 | B2 | 2/2016 | Digiore et al. |
| 9,265,465 | B2 | 2/2016 | Najafi et al. |
| 9,265,928 | B2 | 2/2016 | Pellinen et al. |
| 9,283,375 | B2 | 3/2016 | Moffitt et al. |
| 9,289,151 | B2 | 3/2016 | Kipke et al. |
| 9,289,596 | B2 | 3/2016 | Leven |
| 9,295,830 | B2 | 3/2016 | Pianca |
| 9,314,614 | B2 | 4/2016 | Bedenbaugh |

(56) References Cited

U.S. PATENT DOCUMENTS

| | | |
|---|---|---|
| 9,358,398 B2 | 6/2016 | Moffitt et al. |
| 9,364,659 B1 | 6/2016 | Rao |
| 9,381,347 B2 | 7/2016 | Howard et al. |
| 9,381,348 B2 | 7/2016 | Romero et al. |
| 9,381,356 B2 | 7/2016 | Parker et al. |
| 9,399,128 B2 | 7/2016 | Tooker et al. |
| 9,403,011 B2 | 8/2016 | Mercanzini |
| 9,427,567 B2 | 8/2016 | Romero |
| 9,440,082 B2 | 9/2016 | Mercanzini et al. |
| 9,474,894 B2 | 10/2016 | Mercanzini et al. |
| 9,474,895 B2 | 10/2016 | Digiore et al. |
| 9,498,620 B2 | 11/2016 | Romero et al. |
| 9,517,020 B2 | 12/2016 | Shacham-Diamand et al. |
| 9,592,377 B2 | 3/2017 | Greenberg et al. |
| 9,604,051 B2 | 3/2017 | Vetter et al. |
| 9,662,494 B2 | 5/2017 | Young |
| 9,700,715 B2 | 7/2017 | Dou |
| 9,743,878 B2 | 8/2017 | Drew |
| 9,775,983 B2 | 10/2017 | Digiore et al. |
| 9,775,988 B2 | 10/2017 | Govea et al. |
| 9,827,413 B2 | 11/2017 | Barker et al. |
| 9,833,611 B2 | 12/2017 | Govea et al. |
| 9,855,428 B2 | 1/2018 | Henry et al. |
| 9,861,288 B2 | 1/2018 | Ma et al. |
| 9,925,368 B2 | 3/2018 | Ryu et al. |
| 10,046,165 B2 | 8/2018 | Frewin et al. |
| 10,441,779 B2 | 10/2019 | Mercanzini et al. |
| 2001/0051802 A1 | 12/2001 | Woloszko et al. |
| 2001/0051819 A1 | 12/2001 | Fischell et al. |
| 2002/0062143 A1 | 5/2002 | Baudino et al. |
| 2002/0116042 A1 | 8/2002 | Boling |
| 2003/0004553 A1 | 1/2003 | Grill et al. |
| 2003/0023282 A1 | 1/2003 | Barrett et al. |
| 2003/0036780 A1 | 2/2003 | Barrett et al. |
| 2003/0040785 A1 | 2/2003 | Maschino et al. |
| 2003/0060822 A1 | 3/2003 | Schaer et al. |
| 2003/0083724 A1 | 5/2003 | Jog et al. |
| 2003/0100823 A1 | 5/2003 | Kipke et al. |
| 2003/0135253 A1 | 7/2003 | Kokones et al. |
| 2003/0176892 A1 | 9/2003 | Shalev |
| 2004/0002635 A1 | 1/2004 | Hargrove et al. |
| 2004/0015205 A1 | 1/2004 | Whitehurst et al. |
| 2004/0039434 A1 | 2/2004 | Schrom et al. |
| 2004/0098074 A1 | 5/2004 | Erickson et al. |
| 2004/0102828 A1 | 5/2004 | Lowry et al. |
| 2004/0122335 A1 | 6/2004 | Sackellares et al. |
| 2004/0133390 A1 | 7/2004 | Osorio et al. |
| 2004/0138517 A1 | 7/2004 | Osorio et al. |
| 2004/0138536 A1 | 7/2004 | Frei et al. |
| 2004/0138720 A1 | 7/2004 | Naisberg et al. |
| 2004/0138722 A1 | 7/2004 | Carroll et al. |
| 2004/0152958 A1 | 8/2004 | Frei et al. |
| 2004/0172089 A1 | 9/2004 | Whitehurst et al. |
| 2004/0193021 A1 | 9/2004 | Zdeblick et al. |
| 2004/0215288 A1 | 10/2004 | Lee et al. |
| 2004/0220637 A1 | 11/2004 | Zdeblick et al. |
| 2004/0225335 A1 | 11/2004 | Whitehurst et al. |
| 2004/0243011 A1 | 12/2004 | Plaza |
| 2004/0249417 A1 | 12/2004 | Ransbury et al. |
| 2004/0254483 A1 | 12/2004 | Zdeblick et al. |
| 2005/0004627 A1 | 1/2005 | Gibson et al. |
| 2005/0008660 A1 | 1/2005 | Kipke et al. |
| 2005/0010261 A1 | 1/2005 | Luders et al. |
| 2005/0021103 A1 | 1/2005 | DiLorenzo |
| 2005/0027284 A1 | 2/2005 | Lozano et al. |
| 2005/0033136 A1 | 2/2005 | Govari et al. |
| 2005/0038489 A1 | 2/2005 | Grill |
| 2005/0049655 A1 | 3/2005 | Boveja et al. |
| 2005/0060007 A1 | 3/2005 | Goetz |
| 2005/0060010 A1 | 3/2005 | Goetz |
| 2005/0070971 A1 | 3/2005 | Fowler et al. |
| 2005/0070972 A1 | 3/2005 | Wahlstrand et al. |
| 2005/0075681 A1 | 4/2005 | Rezai et al. |
| 2005/0113882 A1 | 5/2005 | Cameron et al. |
| 2005/0137647 A1 | 6/2005 | Wallace et al. |
| 2005/0143790 A1 | 6/2005 | Kipke et al. |
| 2005/0154419 A1 | 7/2005 | Whitehurst et al. |
| 2005/0154425 A1 | 7/2005 | Boveja et al. |
| 2005/0171522 A1 | 8/2005 | Christopherson |
| 2005/0171558 A1 | 8/2005 | Abovitz et al. |
| 2005/0182455 A1 | 8/2005 | Thrope et al. |
| 2005/0209511 A1 | 9/2005 | Heruth et al. |
| 2005/0209513 A1 | 9/2005 | Heruth et al. |
| 2005/0209643 A1 | 9/2005 | Heruth et al. |
| 2005/0222642 A1 | 10/2005 | Przybyszewski et al. |
| 2005/0240242 A1 | 10/2005 | DiLorenzo |
| 2005/0245988 A1 | 11/2005 | Miesel |
| 2006/0004422 A1 | 1/2006 | De Ridder |
| 2006/0015153 A1 | 1/2006 | Gliner et al. |
| 2006/0030897 A1 | 2/2006 | Gilmer et al. |
| 2006/0041295 A1 | 2/2006 | Osypka |
| 2006/0049957 A1 | 3/2006 | Surgenor et al. |
| 2006/0058588 A1 | 3/2006 | Zdeblick |
| 2006/0058727 A1 | 3/2006 | Bernabei |
| 2006/0058855 A1 | 3/2006 | Gill |
| 2006/0084965 A1 | 4/2006 | Young |
| 2006/0095029 A1 | 5/2006 | Young et al. |
| 2006/0095105 A1 | 5/2006 | Jog et al. |
| 2006/0116581 A1 | 6/2006 | Zdeblick et al. |
| 2006/0129203 A1 | 6/2006 | Garabedian et al. |
| 2006/0135877 A1 | 6/2006 | Giftakis |
| 2006/0149336 A1 | 7/2006 | Meadows |
| 2006/0149337 A1 | 7/2006 | John |
| 2006/0149340 A1 | 7/2006 | Karunasiri |
| 2006/0167497 A1 | 7/2006 | Armstrong et al. |
| 2006/0173263 A1 | 8/2006 | He et al. |
| 2006/0173510 A1 | 8/2006 | Besio et al. |
| 2006/0178709 A1 | 8/2006 | Foster et al. |
| 2006/0184060 A1 | 8/2006 | Belalcazar et al. |
| 2006/0195154 A1 | 8/2006 | Jaax et al. |
| 2006/0200206 A1 | 9/2006 | Firlik et al. |
| 2006/0212090 A1 | 9/2006 | Lozano et al. |
| 2006/0241717 A1 | 10/2006 | Whitehurst et al. |
| 2006/0258951 A1 | 11/2006 | Bleich et al. |
| 2006/0264777 A1 | 11/2006 | Drew |
| 2006/0265022 A1 | 11/2006 | John et al. |
| 2006/0276866 A1 | 12/2006 | McCreery |
| 2006/0282014 A1 | 12/2006 | Kipke et al. |
| 2006/0293720 A1 | 12/2006 | DiLorenzo |
| 2006/0293721 A1 | 12/2006 | Tarver et al. |
| 2007/0027498 A1 | 2/2007 | Maschino et al. |
| 2007/0027500 A1 | 2/2007 | Maschino et al. |
| 2007/0027514 A1 | 2/2007 | Gerber |
| 2007/0043268 A1 | 2/2007 | Russell |
| 2007/0060974 A1 | 3/2007 | Lozano |
| 2007/0067002 A1 | 3/2007 | Lozano |
| 2007/0067003 A1 | 3/2007 | Sanchez et al. |
| 2007/0088403 A1 | 4/2007 | Wyler et al. |
| 2007/0088404 A1 | 4/2007 | Wyler et al. |
| 2007/0093870 A1 | 4/2007 | Maschino |
| 2007/0100389 A1 | 5/2007 | Jaax et al. |
| 2007/0100392 A1 | 5/2007 | Maschino et al. |
| 2007/0100393 A1 | 5/2007 | Whitehurst et al. |
| 2007/0100398 A1 | 5/2007 | Sloan |
| 2007/0106143 A1 | 5/2007 | Flaherty |
| 2007/0123765 A1 | 5/2007 | Hetke et al. |
| 2007/0123944 A1 | 5/2007 | Zdeblick |
| 2007/0135721 A1 | 6/2007 | Zdeblick |
| 2007/0142872 A1 | 6/2007 | Mickle et al. |
| 2007/0150024 A1 | 6/2007 | Leyde et al. |
| 2007/0173890 A1 | 7/2007 | Armstrong |
| 2007/0173896 A1 | 7/2007 | Zdeblick |
| 2007/0173897 A1 | 7/2007 | Zdeblick |
| 2007/0173901 A1 | 7/2007 | Reeve |
| 2007/0173908 A1 | 7/2007 | Begnaud |
| 2007/0179558 A1 | 8/2007 | Gliner et al. |
| 2007/0179569 A1 | 8/2007 | Zdeblick |
| 2007/0185537 A1 | 8/2007 | Zdeblick |
| 2007/0185544 A1 | 8/2007 | Dawant et al. |
| 2007/0185548 A1 | 8/2007 | Zdeblick |
| 2007/0185549 A1 | 8/2007 | Zdeblick |
| 2007/0197892 A1 | 8/2007 | Shen et al. |
| 2007/0203537 A1 | 8/2007 | Goetz et al. |
| 2007/0203546 A1 | 8/2007 | Stone et al. |

(56) References Cited

U.S. PATENT DOCUMENTS

| | | |
|---|---|---|
| 2007/0208394 A1 | 9/2007 | King et al. |
| 2007/0213784 A1 | 9/2007 | Pless |
| 2007/0213785 A1 | 9/2007 | Osorio et al. |
| 2007/0213786 A1 | 9/2007 | Sackellares et al. |
| 2007/0219591 A1 | 9/2007 | Zdeblick et al. |
| 2007/0225674 A1 | 9/2007 | Molnar et al. |
| 2007/0225773 A1 | 9/2007 | Shen et al. |
| 2007/0225774 A1 | 9/2007 | Eskandar et al. |
| 2007/0233192 A1 | 10/2007 | Craig |
| 2007/0249953 A1 | 10/2007 | Frei et al. |
| 2007/0249954 A1 | 10/2007 | Virag et al. |
| 2007/0250133 A1 | 10/2007 | Carlson et al. |
| 2007/0255323 A1 | 11/2007 | Werder et al. |
| 2007/0255338 A1 | 11/2007 | Wahlstrand |
| 2007/0255374 A1 | 11/2007 | Kolafa et al. |
| 2007/0255531 A1 | 11/2007 | Drew |
| 2007/0265683 A1 | 11/2007 | Ehrlich |
| 2007/0282389 A1 | 12/2007 | Moxon et al. |
| 2007/0293908 A1 | 12/2007 | Cowan et al. |
| 2008/0021514 A1 | 1/2008 | Pless |
| 2008/0021517 A1 | 1/2008 | Dietrich |
| 2008/0027289 A1 | 1/2008 | Zdeblick |
| 2008/0027487 A1 | 1/2008 | Patel et al. |
| 2008/0027503 A1 | 1/2008 | Marrosu et al. |
| 2008/0027504 A1 | 1/2008 | Bedenbaugh |
| 2008/0027514 A1 | 1/2008 | DeMulling et al. |
| 2008/0027540 A1 | 1/2008 | Cumming |
| 2008/0039895 A1 | 2/2008 | Fowler et al. |
| 2008/0046012 A1 | 2/2008 | Covalin et al. |
| 2008/0046013 A1 | 2/2008 | Lozano |
| 2008/0058630 A1 | 3/2008 | Robertson |
| 2008/0077186 A1 | 3/2008 | Thompson et al. |
| 2008/0077191 A1 | 3/2008 | Morrell |
| 2008/0103547 A1 | 5/2008 | Okun et al. |
| 2008/0103548 A1 | 5/2008 | Fowler et al. |
| 2008/0103578 A1 | 5/2008 | Gerber |
| 2008/0114417 A1 | 5/2008 | Leyde |
| 2008/0119900 A1 | 5/2008 | DiLorenzo |
| 2008/0139870 A1 | 6/2008 | Gliner et al. |
| 2008/0140152 A1 | 6/2008 | Imran et al. |
| 2008/0154328 A1 | 6/2008 | Thompson et al. |
| 2008/0154331 A1 | 6/2008 | John et al. |
| 2008/0154340 A1 | 6/2008 | Goetz et al. |
| 2008/0161881 A1 | 7/2008 | Firlik et al. |
| 2008/0161896 A1 | 7/2008 | Sauter-Starace et al. |
| 2008/0172103 A1 | 7/2008 | Kao et al. |
| 2008/0177196 A1 | 7/2008 | Burdick et al. |
| 2008/0188905 A1 | 8/2008 | Swartz |
| 2008/0195166 A1 | 8/2008 | Sun et al. |
| 2008/0195227 A1 | 8/2008 | Boling et al. |
| 2008/0208283 A1 | 8/2008 | Vetter et al. |
| 2008/0208287 A1 | 8/2008 | Palermo et al. |
| 2008/0210592 A1 | 9/2008 | Anderson et al. |
| 2008/0215125 A1 | 9/2008 | Farah et al. |
| 2008/0221642 A1 | 9/2008 | Humayun et al. |
| 2008/0242976 A1 | 10/2008 | Robertson et al. |
| 2008/0255439 A1 | 10/2008 | Tang et al. |
| 2008/0255629 A1 | 10/2008 | Jenson et al. |
| 2008/0255647 A1 | 10/2008 | Jensen et al. |
| 2008/0269835 A1 | 10/2008 | Carlson et al. |
| 2008/0269842 A1 | 10/2008 | Giftakis et al. |
| 2008/0269854 A1 | 10/2008 | Hegland et al. |
| 2008/0275526 A1 | 11/2008 | Lozano |
| 2008/0284599 A1 | 11/2008 | Zdeblick et al. |
| 2008/0294218 A1 | 11/2008 | Savage et al. |
| 2008/0300652 A1 | 12/2008 | Lim et al. |
| 2008/0306394 A1 | 12/2008 | Zdeblick et al. |
| 2008/0312726 A1 | 12/2008 | Frank et al. |
| 2008/0316020 A1 | 12/2008 | Robertson et al. |
| 2009/0027504 A1 | 1/2009 | Lim et al. |
| 2009/0062879 A1 | 3/2009 | Li et al. |
| 2009/0082645 A1 | 3/2009 | Hafezi et al. |
| 2009/0105784 A1 | 4/2009 | Massoud-Ansari et al. |
| 2009/0118806 A1 | 5/2009 | Vetter et al. |
| 2009/0132042 A1 | 5/2009 | Hetke et al. |
| 2009/0171416 A1 | 7/2009 | Firlik et al. |
| 2009/0177144 A1 | 7/2009 | Masmanidis et al. |
| 2009/0187196 A1 | 7/2009 | Vetter |
| 2009/0204183 A1 | 8/2009 | Kreidler et al. |
| 2009/0240314 A1 | 9/2009 | Kong et al. |
| 2009/0248122 A1 | 10/2009 | Pianca |
| 2009/0253977 A1 | 10/2009 | Kipke et al. |
| 2009/0256702 A1 | 10/2009 | Robertson et al. |
| 2009/0292325 A1 | 11/2009 | Cederna et al. |
| 2009/0299174 A1 | 12/2009 | Wright et al. |
| 2009/0306728 A1 | 12/2009 | Wright et al. |
| 2009/0306729 A1 | 12/2009 | Doerr |
| 2009/0312770 A1 | 12/2009 | Kozai et al. |
| 2009/0318824 A1 | 12/2009 | Nishida et al. |
| 2009/0325424 A1 | 12/2009 | Aarts et al. |
| 2010/0014541 A1 | 1/2010 | Harriman |
| 2010/0015274 A1 | 1/2010 | Fill |
| 2010/0030298 A1 | 2/2010 | Martens et al. |
| 2010/0036468 A1 | 2/2010 | Decre et al. |
| 2010/0047376 A1 | 2/2010 | Imbeau et al. |
| 2010/0069717 A1 | 3/2010 | Hafezi et al. |
| 2010/0076508 A1 | 3/2010 | McDonald et al. |
| 2010/0076536 A1 | 3/2010 | Merz et al. |
| 2010/0087853 A1 | 4/2010 | Kipke et al. |
| 2010/0100152 A1 | 4/2010 | Martens et al. |
| 2010/0106178 A1 | 4/2010 | Obermiller et al. |
| 2010/0114193 A1 | 5/2010 | Lozano et al. |
| 2010/0114234 A1 | 5/2010 | Zdeblick |
| 2010/0114250 A1 | 5/2010 | Zdeblick |
| 2010/0130844 A1 | 5/2010 | Williams et al. |
| 2010/0145216 A1 | 6/2010 | He et al. |
| 2010/0145414 A1 | 6/2010 | Decre et al. |
| 2010/0152747 A1 | 6/2010 | Padiy et al. |
| 2010/0198315 A1 | 8/2010 | Martens et al. |
| 2010/0249883 A1 | 9/2010 | Zdeblick |
| 2010/0274305 A1 | 10/2010 | Gliner et al. |
| 2010/0292602 A1 | 11/2010 | Worrell et al. |
| 2010/0298908 A1 | 11/2010 | Vardiman |
| 2010/0298917 A1 | 11/2010 | Vardiman |
| 2010/0298918 A1 | 11/2010 | Vardiman |
| 2010/0312188 A1 | 12/2010 | Robertson et al. |
| 2010/0312228 A1 | 12/2010 | Zdeblick et al. |
| 2010/0318163 A1 | 12/2010 | Zdeblick |
| 2010/0331807 A1 | 12/2010 | Whitehurst et al. |
| 2011/0001488 A1 | 1/2011 | Behzadi et al. |
| 2011/0022124 A1 | 1/2011 | Zdeblick et al. |
| 2011/0034964 A1 | 2/2011 | Bi et al. |
| 2011/0034970 A1 | 2/2011 | Barker |
| 2011/0040203 A1 | 2/2011 | Savage et al. |
| 2011/0071766 A1 | 3/2011 | Dolan et al. |
| 2011/0093045 A1 | 4/2011 | Moffitt |
| 2011/0130809 A1 | 6/2011 | Zdeblick |
| 2011/0152988 A1 | 6/2011 | Whitehurst et al. |
| 2011/0154655 A1 | 6/2011 | Hetke et al. |
| 2011/0184495 A1 | 7/2011 | Wang et al. |
| 2011/0190860 A1 | 8/2011 | Harberts et al. |
| 2011/0196454 A1 | 8/2011 | Strand et al. |
| 2011/0208225 A1 | 8/2011 | Martens et al. |
| 2011/0213382 A1 | 9/2011 | Decre et al. |
| 2011/0218417 A1 | 9/2011 | Boogaard et al. |
| 2011/0224757 A1 | 9/2011 | Zdeblick et al. |
| 2011/0224765 A1 | 9/2011 | Harberts et al. |
| 2011/0224766 A1 | 9/2011 | Tol et al. |
| 2011/0282179 A1 | 11/2011 | Zdeblick |
| 2011/0301665 A1 | 12/2011 | Mercanzini et al. |
| 2012/0004520 A1 | 1/2012 | Whitworth et al. |
| 2012/0004527 A1 | 1/2012 | Thompson et al. |
| 2012/0004716 A1 | 1/2012 | Langhammer et al. |
| 2012/0007734 A1 | 1/2012 | Berkman et al. |
| 2012/0022341 A1 | 1/2012 | Zdeblick |
| 2012/0035684 A1 | 2/2012 | Thompson et al. |
| 2012/0053344 A1 | 3/2012 | Lagos Gonzalez |
| 2012/0053658 A1 | 3/2012 | Molnar et al. |
| 2012/0059444 A1 | 3/2012 | Pardoel et al. |
| 2012/0062379 A1 | 3/2012 | Hafezi et al. |
| 2012/0095355 A1 | 4/2012 | Zdeblick |
| 2012/0109262 A1 | 5/2012 | Martens |
| 2012/0109599 A1 | 5/2012 | Martens |
| 2012/0116188 A1 | 5/2012 | Frank et al. |

(56) References Cited

U.S. PATENT DOCUMENTS

| | | | |
|---|---|---|---|
| 2012/0136420 A1 | 5/2012 | Pardoel et al. |
| 2012/0150256 A1 | 6/2012 | Martens |
| 2012/0184837 A1 | 7/2012 | Martens et al. |
| 2012/0253442 A1 | 10/2012 | Gliner et al. |
| 2012/0277819 A1 | 11/2012 | Cowley et al. |
| 2012/0277821 A1 | 11/2012 | Martens et al. |
| 2012/0296444 A1 | 11/2012 | Greenberg et al. |
| 2012/0302912 A1 | 11/2012 | Moffitt et al. |
| 2012/0303087 A1 | 11/2012 | Moffitt et al. |
| 2012/0303088 A1 | 11/2012 | Van Kaam et al. |
| 2012/0303089 A1 | 11/2012 | Martens et al. |
| 2012/0303107 A1 | 11/2012 | Decre et al. |
| 2012/0316630 A1 | 12/2012 | Firlik et al. |
| 2013/0009691 A1 | 1/2013 | Blanken et al. |
| 2013/0030366 A1 | 1/2013 | Robertson et al. |
| 2013/0046356 A1 | 2/2013 | Jensen et al. |
| 2013/0060102 A1 | 3/2013 | Zdeblick |
| 2013/0085361 A1 | 4/2013 | Mercanzini et al. |
| 2013/0131754 A1 | 5/2013 | Sarvazyan |
| 2013/0144132 A1 | 6/2013 | Hafezi et al. |
| 2013/0172716 A1 | 7/2013 | Lozano et al. |
| 2013/0193950 A1 | 8/2013 | Hafezi et al. |
| 2013/0204318 A1 | 8/2013 | Young |
| 2013/0223028 A1 | 8/2013 | Arne et al. |
| 2013/0231188 A1 | 9/2013 | Berberich et al. |
| 2013/0282090 A1 | 10/2013 | Decre et al. |
| 2013/0345780 A1 | 12/2013 | Tabada et al. |
| 2013/0345789 A1 | 12/2013 | Havel et al. |
| 2014/0039578 A1 | 2/2014 | Whitehurst et al. |
| 2014/0066999 A1 | 3/2014 | Carcieri et al. |
| 2014/0200633 A1 | 7/2014 | Moffitt |
| 2014/0277284 A1 | 9/2014 | Chen et al. |
| 2014/0343652 A1 | 11/2014 | Rosenberg et al. |
| 2015/0051678 A1 | 2/2015 | Reed et al. |
| 2015/0105774 A1 | 4/2015 | Lindquist et al. |
| 2015/0142090 A1 | 5/2015 | Duijsens et al. |
| 2015/0151111 A1 | 6/2015 | Pianca et al. |
| 2015/0209578 A1 | 7/2015 | Kast et al. |
| 2015/0246233 A1 | 9/2015 | Kaemmerer |
| 2015/0290452 A1 | 10/2015 | Kokones et al. |
| 2015/0335258 A1 | 11/2015 | Masmanidis |
| 2015/0355413 A1 | 12/2015 | Bhagavatula et al. |
| 2015/0360023 A1 | 12/2015 | Howard et al. |
| 2016/0008592 A1 | 1/2016 | Romero et al. |
| 2016/0023003 A1 | 1/2016 | Perryman et al. |
| 2016/0059016 A1 | 3/2016 | Mercanzini |
| 2016/0074651 A1 | 3/2016 | Moffitt et al. |
| 2016/0144186 A1 | 5/2016 | Kaemmerer et al. |
| 2016/0228706 A1 | 8/2016 | Hershey et al. |
| 2016/0331953 A1 | 11/2016 | Reed et al. |
| 2016/0331975 A1 | 11/2016 | Henry et al. |
| 2016/0361535 A1 | 12/2016 | Perryman et al. |
| 2017/0007813 A1 | 1/2017 | Negi et al. |
| 2017/0049345 A1 | 2/2017 | Single |
| 2017/0136238 A1 | 5/2017 | Hartig et al. |
| 2017/0143982 A1 | 5/2017 | Mercanzini |
| 2017/0189700 A1 | 7/2017 | Moffitt et al. |
| 2017/0197086 A1 | 7/2017 | Howard et al. |
| 2017/0266432 A1 | 9/2017 | Seeley et al. |
| 2017/0296808 A1 | 10/2017 | Greenberg et al. |
| 2017/0361101 A1 | 12/2017 | Single |
| 2018/0154156 A1 | 6/2018 | Clark et al. |
| 2018/0185656 A1 | 7/2018 | Shepard et al. |
| 2018/0272142 A1 | 9/2018 | Zhang et al. |
| 2020/0009372 A1 | 1/2020 | Mercanzini et al. |

FOREIGN PATENT DOCUMENTS

| | | |
|---|---|---|
| CN | 101600470 A | 12/2009 |
| CN | 201871104 U | 6/2011 |
| CN | 102274074 A | 12/2011 |
| CN | 102341036 A | 2/2012 |
| CN | 103619405 A | 3/2014 |
| EP | 0 586 664 A1 | 3/1994 |
| EP | 0 677 743 | 10/1995 |
| EP | 0 743 839 | 11/1996 |
| EP | 0 892 654 | 1/1999 |
| EP | 0 895 483 | 2/1999 |
| EP | 0 959 942 | 12/1999 |
| EP | 1 048 319 | 11/2000 |
| EP | 1 062 973 | 12/2000 |
| EP | 1 102 607 | 5/2001 |
| EP | 1 257 320 | 11/2002 |
| EP | 1 446 189 | 8/2004 |
| EP | 1 514 576 | 3/2005 |
| EP | 1 750 798 | 2/2007 |
| EP | 1 890 764 | 2/2008 |
| EP | 1 931 419 | 6/2008 |
| EP | 1 985 579 | 10/2008 |
| EP | 1 993 665 | 11/2008 |
| EP | 2 046 441 | 4/2009 |
| EP | 2 066 396 B1 | 6/2009 |
| EP | 2 069 003 | 6/2009 |
| EP | 2 131 916 | 12/2009 |
| EP | 2 144 665 A1 | 1/2010 |
| EP | 2 167 188 | 3/2010 |
| EP | 2 320 221 A1 | 5/2011 |
| EP | 2 341 979 | 7/2011 |
| EP | 2 389 975 B1 | 11/2011 |
| EP | 2 456 513 A1 | 5/2012 |
| EP | 2 476 453 A1 | 7/2012 |
| EP | 2 542 303 A1 | 1/2013 |
| EP | 2 559 454 A1 | 2/2013 |
| EP | 2 604 313 A1 | 6/2013 |
| EP | 2 618 889 | 7/2013 |
| EP | 2 620 179 A1 | 7/2013 |
| EP | 2 623 154 A1 | 8/2013 |
| EP | 2 626 108 A1 | 8/2013 |
| EP | 2 626 109 A1 | 8/2013 |
| EP | 2 626 110 A1 | 8/2013 |
| EP | 2 626 111 A1 | 8/2013 |
| EP | 2 656 875 A1 | 10/2013 |
| EP | 2 656 876 A1 | 10/2013 |
| EP | 2 664 354 B1 | 11/2013 |
| EP | 2 674 193 A1 | 12/2013 |
| EP | 2 862 595 B1 | 4/2015 |
| EP | 3 111 835 A1 | 1/2017 |
| EP | 3 231 476 A1 | 10/2017 |
| JP | 2005-052647 | 3/2005 |
| JP | 2012-179333 A | 9/2012 |
| JP | 2017-525546 A | 9/2017 |
| WO | WO-98/10010 | 3/1998 |
| WO | WO-02/068042 A1 | 9/2002 |
| WO | WO-03/022354 | 3/2003 |
| WO | WO-03/028521 | 4/2003 |
| WO | WO-03/066153 A2 | 8/2003 |
| WO | WO-03/066157 | 8/2003 |
| WO | WO-2004/043536 A1 | 5/2004 |
| WO | WO-2018/068013 A1 | 5/2004 |
| WO | WO-2004/045707 | 6/2004 |
| WO | WO-2005/002467 | 1/2005 |
| WO | WO-2005/067792 | 7/2005 |
| WO | WO-2005/112216 | 11/2005 |
| WO | WO-2006/029257 | 3/2006 |
| WO | WO-2006/047264 A1 | 5/2006 |
| WO | WO-2006/047265 A2 | 5/2006 |
| WO | WO-2006/104432 | 10/2006 |
| WO | WO-2007/002144 | 1/2007 |
| WO | WO-2007/009070 | 1/2007 |
| WO | WO-2007/011611 | 1/2007 |
| WO | WO-2007/025356 | 3/2007 |
| WO | WO-2007/028003 A2 | 3/2007 |
| WO | WO-2007/042999 A2 | 4/2007 |
| WO | WO-2007/092330 A1 | 8/2007 |
| WO | WO-2007/100428 | 9/2007 |
| WO | WO-2007/108718 | 9/2007 |
| WO | WO-2008/003318 | 1/2008 |
| WO | WO-2008/005478 | 1/2008 |
| WO | WO-2008/016881 | 2/2008 |
| WO | WO-2008/035285 | 3/2008 |
| WO | WO-2008/035344 | 3/2008 |
| WO | WO-2008/051463 | 5/2008 |
| WO | WO-2008/064269 A2 | 5/2008 |
| WO | WO-2008/068759 | 6/2008 |

(56) References Cited

FOREIGN PATENT DOCUMENTS

| WO | WO-2008/075294 | 6/2008 |
|---|---|---|
| WO | WO-2008/077440 | 7/2008 |
| WO | WO-2008/088897 | 7/2008 |
| WO | WO-2008/089726 | 7/2008 |
| WO | WO-2008/107822 | 9/2008 |
| WO | WO-2008/109298 | 9/2008 |
| WO | WO-2008/133616 | 11/2008 |
| WO | WO-2008/133683 | 11/2008 |
| WO | WO-2008/138305 | 11/2008 |
| WO | WO-2010/014686 | 2/2010 |
| WO | WO-2010/055421 A1 | 5/2010 |
| WO | WO-2011/000791 A1 | 1/2011 |
| WO | WO-2011/115999 | 9/2011 |
| WO | WO-2013/014206 A1 | 1/2013 |
| WO | WO-2016/030823 | 3/2016 |
| WO | WO-2017/203301 A1 | 11/2017 |

OTHER PUBLICATIONS

US 8,469,885 B2, 06/2013, Hafezi et al. (withdrawn)
Advisory Action on U.S. Appl. No. 15/962,632 dated Jul. 7, 2022.
Foreign Search Report on EP 21207327.4 dated Feb. 9, 2022.
International Search Report on PCT/IB2022/059612 dated Jan. 2, 2023.
Non-Final Office Action on U.S. Appl. No. 15/962,632 dated Nov. 25, 2022.
Non-Final Office Action on U.S. Appl. No. 16/899,820 dated Dec. 23, 2022.
Final Office Action on U.S. Appl. No. 15/962,632 dated Apr. 1, 2022.
AU Examination Report on AU 2011234422 dated Feb. 11, 2014 (3 pages).
Benabid et al., "Combined (Thalamotomy and Stimulation) Stereotactic Surgery of the VIM Thalamic Nucleus for Bilateral Parkinson Disease", Proceedings of the Meeting of the American Society for Stereotactic and Functional Neurosurgery, vol. 50, Montreal 1987 Appl. Neurophysiol., pp. 344-346 (3 pages).
Bucher et al., "Low-impedance thin-film polycrystalline silicon microelectrodes for extracellular stimulation and recording", Biosensors & Bioelectronics, vol. 14, 1999, pp. 639-649 (11 pages).
Chinese Office Action on CN 201580019701.2 dated Aug. 17, 2020 (9 pages).
Cogan et al., "Plasma-enhanced chemical vapor deposited silicon carbide as an implantable dielectric coating", Journal of Biomedical Materials Research Part A 67.3, 2003, pp. 856-867 (12 pages).
Communication from the European Patent Office on EP 09795810.2 dated Sep. 14, 2011 (2 pages).
Corrected Notice of Allowability on U.S. Appl. No. 14/470,356 dated May 18, 2016 (6 pages).
Decision of Rejection and Decision for Dismissal of Amendment on JP 2011-543841 dated May 15, 2014 (6 pages).
Decision of Rejection for JP 2012-541491 dated Oct. 26, 2015 (7 pages).
EIC Biomedical, "Thin-film Encapsulation for Neural Recording and Stimulation Electrodes", Silicon carbide and oxycarbide, Apr. 2008, pp. 1-2 (2 pages).
EPO Communication and Search Report EP 09795810.2 dated Sep. 25, 2013 (5 pages).
EPO Communication dated May 22, 2013 with Extended Search Report on EP 12198290.4-1652 dated May 13, 2013 (6 pages).
European Search Report on EP 09803534.8 dated Jul. 21, 2011 (5 pages).
European Search Report on EP 13169272.5 dated Aug. 30, 2013 (5 pages).
European Search Report on EP 16190439 dated Jul. 19, 2017 (2 pages).
Examination Report for EP 09795810.2 dated May 8, 2014 (4 pages).
Examination Report on AU 2009276603 dated Mar. 3, 2014 (3 pages).
Examination Report on EP 09795810.2 dated Jun. 22, 2012 (5 pages).
Examination Report on EP 11711884.4 dated Mar. 28, 2014 (4 pages).
Extended European Search Report for EP 19174013.3 dated Oct. 8, 2019 (7 pages).
Extended European Search Report on EP 14172592 dated Aug. 28, 2014 (8 pages).
Extended European Search Report on EP 16190439.6 dated Jul. 27, 2017 (7 pages).
Extended European Search Report on EP 16199868.7 dated Apr. 28, 2017 (7 pages).
Extended European Search Report on EP 18208814.6 dated Mar. 28, 2019 (6 pages).
Extended European Search Report on EP 19165102.5 dated Jul. 8, 2019 (7 pages).
Fierce Medical Devices, "Medtronic Announces First U.S. Implant of World's Smallest, Minimally Invasive Cardiac Pacemaker", Feb. 20, 2014, pp. 1-3 (3 pages).
Final Office Action on U.S. Appl. No. 13/056,261 dated Jan. 9, 2014 (9 pages).
Final Office Action on U.S. Appl. No. 13/128,821 dated Dec. 14, 2012 (17 pages).
Final Office Action on U.S. Appl. No. 13/638,435 dated Jun. 30, 2015 (12 pages).
Final Office Action on U.S. Appl. No. 14/309,491 dated Mar. 3, 2016 (12 pages).
Final Office Action on U.S. Appl. No. 14/731,296 dated Apr. 6, 2017 (8 pages).
Final Office Action on U.S. Appl. No. 15/281,468 dated Jun. 14, 2017 (6 pages).
Final Office Action on U.S. Appl. No. 15/369,766 dated Feb. 23, 2018 (13 pages).
Final Office Action on U.S. Appl. No. 15/369,766 dated Feb. 7, 2019 (9 pages).
Final Office Action on U.S. Appl. No. 16/015,625 dated Dec. 28, 2018 (13 pages).
Final Office Action on U.S. Appl. No. 15/311,082 dated May 26, 2020 (14 pages).
Final Office Action on U.S. Appl. No. 15/962,632 dated Oct. 6, 2020 (13 pages).
First Office Action for CN 201580019701.2 dated Nov. 15, 2019 (18 pages).
First Office Action for CN Appl. No. 201780017009.5, dated Dec. 3, 2021 (with English translation, 14 pages).
Foreign Action other than Search Report on EP 15760291.3 dated Apr. 23, 2021.
Foreign Action other than Search Report on JP 2020-036370 dated Jan. 25, 2021.
Foreign Search Reporton EP 21184317.2 dated Oct. 22, 2021.
Gibney, Michael, "St. Jude places its Nanostim leadless pacemaker in a U.K. patient", Fierce Medical Devices, Jan. 27, 2014, pp. 1-3 (3 pages).
Hosp et al., "Thin-film epidural microelectrode arrays for somatosensory and motor cortex mapping in rat", Journal of Neuroscience Methods, vol. 172, 2008, pp. 255-262 (8 pages).
International Preliminary Report on Patentability and Written Opinion of the International Searching Authority on PCT/IB2017/050551 dated Aug. 16, 2018 (8 pages).
International Preliminary Report on Patentability for PCT/EP2010/068658 dated Jun. 5, 2012 (11 pages).
International Preliminary Report on Patentability on PCT/IB2009/007715 dated May 17, 2011 (9 pages).
International Preliminary Report on Patentability on PCT/IB2015/053610 dated Dec. 1, 2016 (8 pages).
International Preliminary Report on Patentability on PCT/IB2015/056437 dated Mar. 9, 2017 (7 pages).
International Preliminary Report on Patentability on PCT/IB2015/056438 dated Mar. 9, 2017 (7 pages).
International Preliminary Reporton Patentability on PCT/IB2019/051635 dated Sep. 17, 2020 (7 pages).
International Preliminary Report on Patentability on PCT/IB2019/053275 dated Nov. 5, 2020 (8 pages).

(56) References Cited

OTHER PUBLICATIONS

International Preliminary Report on Patentability on PCT/US2009/052077 dated Feb. 1, 2011 (6 pages).
International Search Report and Written Opinion of the International Searching Authority on PCT/IB2019/051635 dated Jun. 3, 2019 (13 pages).
International Search Report and Written Opinion of the International Searching Authority on PCT/IB2019/053275 dated Jul. 4, 2019 (12 pages).
International Search Report and Written Opinion on PCT/EP2010/068658 dated Mar. 21, 2011 (18 pages).
International Search Report and Written Opinion on PCT/EP2011/055045 dated Jul. 18, 2011 (14 pages).
International Search Report and Written Opinion on PCT/IB2015/053610 dated Jul. 20, 2015 (12 pages).
International Search Report and Written Opinion on PCT/IB2015/056437 dated Nov. 5, 2015 (11 pages).
International Search Report and Written Opinion on PCT/IB2015/056438 dated Nov. 5, 2015 (11 pages).
International Search Report and Written Opinion on PCT/IB2017/050551 dated Mar. 29, 2017 (17 pages).
International Search Report and Written Opinion on PCT/US09/52077 dated Sep. 25, 2009 (8 pages).
International Search Report on PCT/IB2009/007715 dated Apr. 22, 2010 (6 pages).
Janders et al., "Novel Thin Film Titanium Nitride Micro-Electrodes With Excellent Charge Transfer Capability for Cell Stimulation and Sensing Applications", 18th Annual International Conference of the IEEE Engineering in Medicine and Biology Society, 1996, Amsterdam (3 pages).
Moxon et al., "Nanostructured Surface Modification of Ceramic-Based Microelectrodes to Enhance Biocompatibility for a Direct Brain-Machine Interface", IEEE Transactions on Biomedical Engineering, vol. 51, No. 6, Jun. 2004, pp. 881-889 (9 pages).
Non-Final Office Action for U.S. Appl. No. 15/311,082 dated Jan. 10, 2020 (14 pages).
Non-Final Office Action for U.S. Appl. No. 15/910,278 dated Nov. 26, 2019 (7 pages).
Non-Final Office Action on U.S. Appl. No. 13/056,261 dated Aug. 7, 2013 (8 pages).
Non-Final Office Action on U.S. Appl. No. 13/128,821 dated Nov. 14, 2013 (8 pages).
Non-Final Office Action on U.S. Appl. No. 13/128,821 dated Apr. 24, 2012 (10 pages).
Non-Final Office Action on U.S. Appl. No. 13/512,936 dated Aug. 14, 2013 (11 pages).
Non-Final Office Action on U.S. Appl. No. 13/638,435 dated Feb. 10, 2016 (12 pages).
Non-Final Office Action on U.S. Appl. No. 13/638,435 dated Mar. 12, 2015 (15 pages).
Non-Final Office Action on U.S. Appl. No. 14/287,917 dated Sep. 26, 2014 (21 pages).
Non-Final Office Action on U.S. Appl. No. 14/309,491 dated Jul. 28, 2015 (13 pages).
Non-Final Office Action on U.S. Appl. No. 14/316,154 dated Dec. 18, 2014 (8 pages).
Non-Final Office Action on U.S. Appl. No. 14/470,423 dated Jan. 21, 2016 (12 pages).
Non-Final Office Action on U.S. Appl. No. 14/731,296 dated Nov. 22, 2017 (9 pages).
Non-Final Office Action on U.S. Appl. No. 14/731,296 dated Oct. 5, 2016 (9 pages).
Non-Final Office Action on U.S. Appl. No. 14/945,952 dated Jul. 26, 2016 (8 pages).
Non-Final Office Action on U.S. Appl. No. 15/185,709 dated Jul. 3, 2018 (17 pages).
Non-Final Office Action on U.S. Appl. No. 15/194,033 dated Aug. 22, 2016 (5 pages).
Non-Final Office Action on U.S. Appl. No. 15/281,468 dated Dec. 7, 2016 (8 pages).
Non-Final Office Action on U.S. Appl. No. 15/369,766 dated Apr. 20, 2017 (12 pages).
Non-Final Office Action on U.S. Appl. No. 15/369,766 dated Jun. 29, 2018 (9 pages).
Non-Final Office Action on U.S. Appl. No. 15/369,766 dated May 31, 2019 (10 pages).
Non-Final Office Action on U.S. Appl. No. 15/426,816 dated Mar. 21, 2017 (8 pages).
Non-Final Office Action on U.S. Appl. No. 15/878,066 dated Mar. 19, 2018 (8 pages).
Non-Final Office Action on U.S. Appl. No. 15/962,632 dated May 12, 2021.
Non-Final Office Action on U.S. Appl. No. 16/015,625 dated Aug. 9, 2018 (14 pages).
Non-Final Office Action on U.S. Appl. No. 15/962,632 dated Mar. 30, 2020 (10 pages).
Non-Final Office Action on U.S. Appl. No. 16/236,716 dated Apr. 29, 2020 (9 pages).
Non-Final Office Action on U.S. Appl. No. 16/551,390 dated Apr. 29, 2021.
Notice of Allowance for U.S. Appl. No. 15/369,766 dated Oct. 17, 2019 (12 pages).
Notice of Allowance on U.S. Appl. No. 13/056,261 dated May 8, 2014 (8 pages).
Notice of Allowance on U.S. Appl. No. 13/128,821 dated Dec. 24, 2013 (6 pages).
Notice of Allowance on U.S. Appl. No. 13/128,821 dated Mar. 25, 2014 (7 pages).
Notice of Allowance on U.S. Appl. No. 13/512,936 dated Feb. 20, 2014 (7 pages).
Notice of Allowance on U.S. Appl. No. 13/512,936 dated Nov. 25, 2013 (7 pages).
Notice of Allowance on U.S. Appl. No. 13/638,435 dated Sep. 16, 2016 (13 pages).
Notice of Allowance on U.S. Appl. No. 14/287,917 dated Apr. 15, 2015 (5 pages).
Notice of Allowance on U.S. Appl. No. 14/287,917 dated Jul. 20, 2015 (5 pages).
Notice of Allowance on U.S. Appl. No. 14/309,491 dated May 11, 2016 (10 pages).
Notice of Allowance on U.S. Appl. No. 14/316,154 dated Apr. 20, 2015 (12 pages).
Notice of Allowance on U.S. Appl. No. 14/470,356 dated Apr. 13, 2016 (9 pages).
Notice of Allowance on U.S. Appl. No. 14/470,356 dated Mar. 18, 2016 (8 pages).
Notice of Allowance on U.S. Appl. No. 14/470,423 dated Jun. 15, 2016 (5 pages).
Notice of Allowance on U.S. Appl. No. 14/731,296 dated Aug. 15, 2018 (7 pages).
Notice of Allowance on U.S. Appl. No. 14/731,296 dated May 7, 2018 (5 pages).
Notice of Allowance on U.S. Appl. No. 14/945,952 dated Dec. 7, 2016 (5 pages).
Notice of Allowance on U.S. Appl. No. 15/185,709 dated Jun. 10, 2019 (2 pages).
Notice of Allowance on U.S. Appl. No. 15/185,709 dated Apr. 26, 2019 (5 pages).
Notice of Allowance on U.S. Appl. No. 15/185,709 dated Nov. 9, 2018 (7 pages).
Notice of Allowance on U.S. Appl. No. 15/194,033 dated Oct. 27, 2016 (7 pages).
Notice of Allowance on U.S. Appl. No. 15/281,468 dated Jun. 1, 2018 (2 pages).
Notice of Allowance on U.S. Appl. No. 15/281,468 dated Feb. 13, 2018 (5 pages).
Notice of Allowance on U.S. Appl. No. 15/281,468 dated Nov. 15, 2017 (8 pages).
Notice of Allowance on U.S. Appl. No. 15/281,468 dated Jul. 27, 2018 (2 pages).
Notice of Allowance on U.S. Appl. No. 15/311,082 dated Dec. 14, 2020.

(56) References Cited

OTHER PUBLICATIONS

Notice of Allowance on U.S. Appl. No. 15/422,393 dated Jul. 11, 2017 (7 pages).
Notice of Allowance on U.S. Appl. No. 15/422,393 dated Aug. 14, 2017 (5 pages).
Notice of Allowance on U.S. Appl. No. 15/422,393 dated Oct. 25, 2017 (5 pages).
Notice of Allowance on U.S. Appl. No. 15/426,816 dated Oct. 12, 2017 (7 pages).
Notice of Allowance on U.S. Appl. No. 15/878,066 dated Oct. 3, 2018 (7 pages).
Notice of Allowance on U.S. Appl. No. 15/878,066 dated Dec. 5, 2018 (2 pages).
Notice of Allowance on U.S. Appl. No. 16/015,625 dated Mar. 28, 2019 (8 pages).
Notice of Allowance on U.S. Appl. No. 16/015,625 dated May 8, 2019 (8 pages).
Notice of Allowance on U.S. Appl. No. 16/236,716 dated Dec. 9, 2020.
Notice of Allowance on U.S. Appl. No. 16/379,710 dated Dec. 15, 2021.
Notice of Allowance on U.S. Appl. No. 16/531,701 dated May 25, 2021.
Notice of Allowance on U.S. Appl. No. 16/901,583 dated Nov. 4, 2021.
Notice of Allowance on U.S. Appl. No. 15/311,082 dated Aug. 4, 2020 (8 pages).
Notice of Allowance on U.S. Appl. No. 15/311,082 dated Sep. 23, 2020 (7 pages).
Notice of Allowance on U.S. Appl. No. 15/369,766 dated Mar. 5, 2020 (8 pages).
Notice of Allowance on U.S. Appl. No. 15/910,278 dated Mar. 9, 2020 (8 pages).
Notice of Allowance on U.S. Appl. No. 16/236,716 dated Aug. 28, 2020 (5 pages).
Notice of Reasons for Rejection on JP 2011-521276 dated Mar. 3, 2014 (6 pages).
Notice of Reasons for Rejection on JP 2011-521276 dated May 30, 2013 (4 pages).
Notice of Reasons for Rejection on JP 2011-543841 dated Oct. 21, 2013 (6 pages).
Notice of Reasons for Rejection on JP 2011-543841 dated May 30, 2013 (4 pages).
Notice of Reasons for Rejection on JP 2017-530450 dated Jul. 11, 2019 (4 pages).
Notice of Reasons for Rejections on JP 2012-541491 dated Aug. 28, 2014 (15 pages).
Office Action for CA 3026948 dated Jan. 15, 2020 (4 pages).
Office Action for EP 10787404.2 dated Mar. 26, 2013 (7 pages).
Office Action issued in Canadian Application No. 3,026,948 dated Jan. 7, 2021.
Office Action on CA 2732309 dated Dec. 7, 2015 (3 pages).
Office Action on CA 2732309 dated Nov. 8, 2016 (4 pages).
Office Action on CA 2743575 dated Jun. 11, 2015 (5 pages).
Office Action on CA 2743575 dated Sep. 14, 2015 (4 pages).
Office Action on CA 2743575 dated Jan. 21, 2015 (4 pages).
Office Action on CA 2743575 dated Sep. 25, 2014 (3 pages).
Office Action on CA 2782710 dated Aug. 14, 2017 (5 pages).
Office Action on CA 2782710 dated Oct. 19, 2016 (4 pages).
Office Action on CA 2795159 dated Dec. 18, 2018 (3 pages).
Office Action on CA 2795159 dated Jan. 27, 2017 (4 pages).
Office Action on CN 201580016170.1 dated Jan. 28, 2019 (10 pages).
Office Action on EP 10787404.2 dated May 6, 2015 (6 pages).
Office Action on EP 14172592.9 dated Aug. 20, 2015 (5 pages).
Office Action on JP 2013-501857 dated Jun. 1, 2015 (8 pages).
Office Action on JP 2013-501857 dated Sep. 17, 2014 (8 pages).
Patent Examination Report No. 1 on AU 2009315316 dated Jan. 31, 2014 (3 pages).
Patent Examination Report No. 1 on AU 2010326613 dated Jan. 30, 2014 (2 pages).
Pollak et al. "Effets de la Stimulation du Noyau Sous-Thalamique Dans La Maladie De Parkinson", Rev. Neurol Paris, vol. 149, No. 3, pp. 175-176, Masson, Paris, 1993 (2 pages).
Rousche et al., "Flexible polyimide-based intracortical electrode arrays with bioactive capability," IEEE Transactions on Biomedical Engineering, vol. 48, No. 3, Mar. 2001, pp. 361-371 (10 pages).
Second Notice of Reasons for Rejection on JP 2012-541491 dated Apr. 8, 2015 (10 pages).
Sepulveda et al., "Finite Element Analysis of Current Pathways with Implanted Electrodes", J. Biomed. Eng., Jan. 1983, vol. 5, pp. 41-48 (8 pages).
U.S. Office Action on U.S. Appl. No. 16/531,701 dated Feb. 26, 2021.
Written Opinion of the International Search Authority on PCT/IB2009/07715 dated May 12, 2011 (8 pages).
Written Opinion on HU 201103393-3 dated May 2, 2012 (10 pages).
Written Opinion on PCT/EP2010/068658 dated Jun. 1, 2012 (10 pages).
Ziaie et al., "A Single-Channel Implantable Microstimulator for Functional Neuromuscular Stimulation", IEEE Transactions on Biomedical Engineering, vol. 44, No. 10, Oct. 1997, pp. 909-920 (12 pages).

NEUROSTIMULATION DEVICE

CROSS-REFERENCE TO RELATED APPLICATIONS

The present application claims priority under 35 U.S.C. § 120 as a continuation of U.S. patent application Ser. No. 16/901,583, titled "NEUROSTIMULATION DEVICE," filed Jun. 15, 2020, which claims priority under 35 U.S.C. § 120 as a continuation of U.S. patent application Ser. No. 15/910,278, titled "NEUROSTIMULATION DEVICE," filed Mar. 2, 2018 and issued on Jul. 7, 2020 as U.S. Pat. No. 10,702,692, each of which is incorporated herein by reference in its entirety.

BACKGROUND OF THE DISCLOSURE

Deep brain stimulation (DBS) can include neurostimulation therapy that involves electrical stimulation systems that stimulate the human brain and body. DBS can be used to treat a number of neurological disorders. DBS can involve electrically stimulating a target area of the brain.

SUMMARY OF THE DISCLOSURE

The present disclosure describes a stimulation device that can be formed into a cylindrical shape. Internally, the stimulation device can include a silicon etched support comb with faces to align, route, and hold wires. The support comb can enable the interconnection of the wires with the microelectrode film that includes the stimulation device's electrodes. The stimulation device can also include an internal support tube that can reduce mechanical detachment of the microelectrode film from its epoxy mold by providing a long edge anchoring system. The microelectrode film can be rolled into a three-dimensional configuration to increase the degrees of freedom during the assembly process.

According to at least one aspect of the disclosure an implantable lead device can include a support comb. The support comb can include an attachment face and a routing face. The routing face can include a plurality of slots. The lead device can include a microelectrode film. The microelectrode film can include a body. The body can include a plurality of electrodes. The microelectrode film can include an extension extending from the body. The extension can include a first face. The first face of the extension can include a plurality of electrical contacts coupled with the plurality of electrodes. The extension can include a second face. The second face of the extension can be coupled with the attachment face of the support comb. The lead device can include a plurality of wires. Each of the plurality of wires can pass through a respective one of the plurality of slots and couple with a respective one of the plurality of electrical contacts.

The attachment face can include a channel to route an adhesive under at least a portion of the second face of the microelectrode film. A first face of the body of the microelectrode film can be coupled with the support tube. The support tube can include a plurality of radio opaque markers that can be aligned with the plurality of electrodes. The support tube can include a plurality of merlons on a first end. The first end can be configured to mate with or receive the support comb.

The lead device can include a support tube that can include a plurality of radio opaque markers. Each of the plurality of wires can be coupled with a respective one of the plurality of electrical contacts via wire bonding.

The extension of the microelectrode film can include a first leg and a second leg. The first leg can include the first face of the extension and the second face of the extension. The second leg can include a plurality of traces coupling a subset of the plurality of electrodes to the plurality of electrical contacts.

The first leg and the second leg of the extension can be rolled around the support comb. The lead device can include an epoxy backfill of the microelectrode film to form a probe shaft.

According to at least one aspect of the disclosure, a method to manufacture an implantable lead device can include providing a support comb. The support comb can include an attachment face and a routing face. The routing face can include a plurality of slots. The method can include coupling a first portion of a microelectrode film with the attachment face of the support comb. The first portion of the microelectrode film can include a plurality of electrical contacts. The method can include positioning each of a plurality of wires through a respective one of the plurality of slots of the routing face. The method can include coupling each of the plurality of wires with a respective one of the plurality of electrical contacts. The method can include rolling a second portion of the microelectrode film about the support comb.

The method can include forming a second portion of the microelectrode film. The second portion can include a plurality of electrodes in electrical communication with the plurality of electrical contacts. The method can include forming a third portion of the microelectrode film. The third portion can include a plurality of electrical traces coupling a portion of the plurality of electrodes to a portion of the plurality of electrical contacts.

The method can include coupling a second portion of the microelectrode film to an outer face of a support tube. The second portion of the microelectrode film can include a plurality of electrodes. The method can include over molding the support comb with an epoxy.

The method can include forming a plurality of radio opaque markers in a support tube. The method can include aligning the plurality of radio opaque markers with a plurality of electrodes formed in the microelectrode film. The plurality of radio opaque markers can be offset from the plurality of electrodes.

The method can include wire bonding each of the plurality of wires with the respective one of the plurality of electrical contacts. The method can include rolling a second portion of the microelectrode film to form a cylinder. The method can include filling the cylinder with an epoxy.

The method can include under filling a channel formed in the attachment face with an epoxy to couple the first portion of the microelectrode film with the attachment face. The method can include etching the support comb in silicon.

The method can include coupling a first edge of the microelectrode film with a second edge of the microelectrode film to form a cylinder. The method can include inserting the first and second edges of the microelectrode film into a slit of a support tube.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Figure 1:
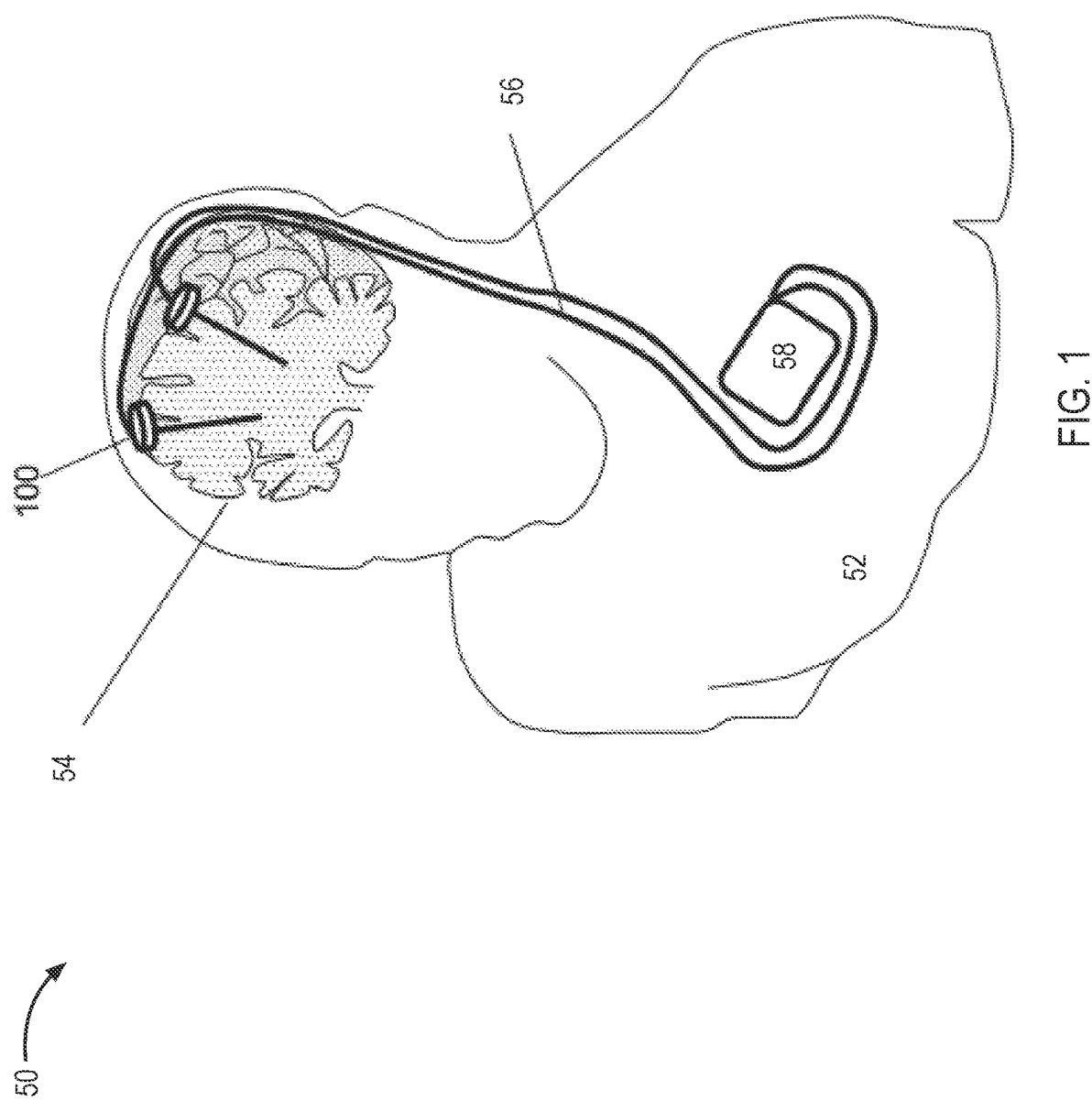
FIG. 1 illustrates an example system to perform neurostimulation.

FIG. 1 illustrates an example system 50 for performing neurostimulation. The system 50 includes a stimulation lead 100 implanted into the brain 54 of a patient 52. The stimulation lead 100 is coupled with a stimulator 58 through cables 56. The stimulator 58 generates therapeutic, electrical stimulations that can be delivered to the patient's brain 54 by the stimulation lead 100. The stimulation lead 100 can be an implantable lead device, which can be chronically or acutely implanted into the patient 52.

Figure 2:
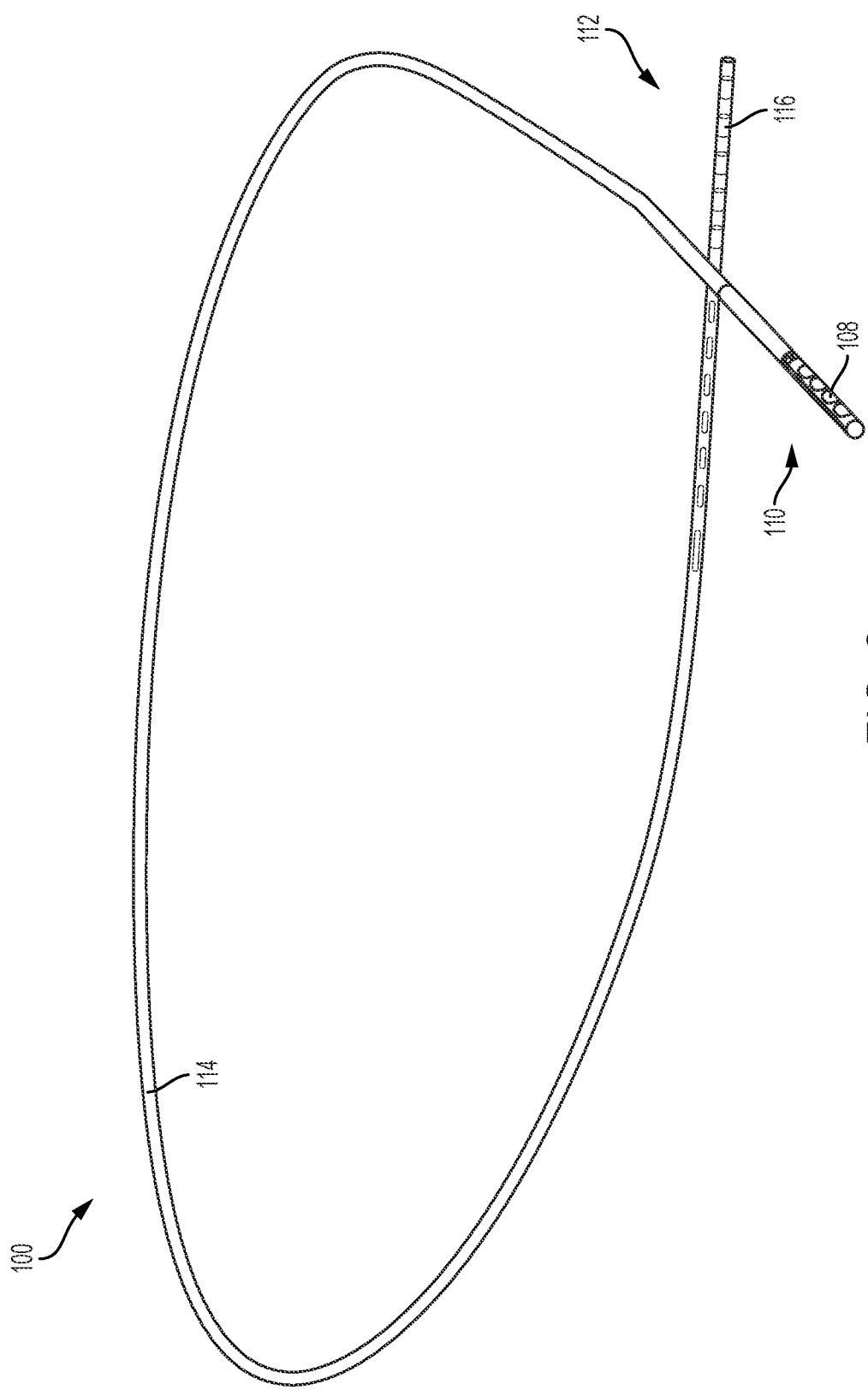
FIG. 2 illustrates the stimulation lead for use in the system illustrated in FIG. 1.

FIG. 2 illustrates the stimulation lead 100. The stimulation lead 100 includes a distal end 110 and a proximal end 112. The distal end 110 includes a plurality of electrodes 108. The proximal end 112 includes a plurality of terminal contacts 116. Each of the terminal contacts 116 are electrically coupled with at least one of the electrodes 108. For example, a wire (or other electrical trace) can run through the interior of the body 114 from one of the terminal contacts 116 to a contact disposed toward the distal end 110 that is in electrical communication with the electrode 108.

Figure 3:
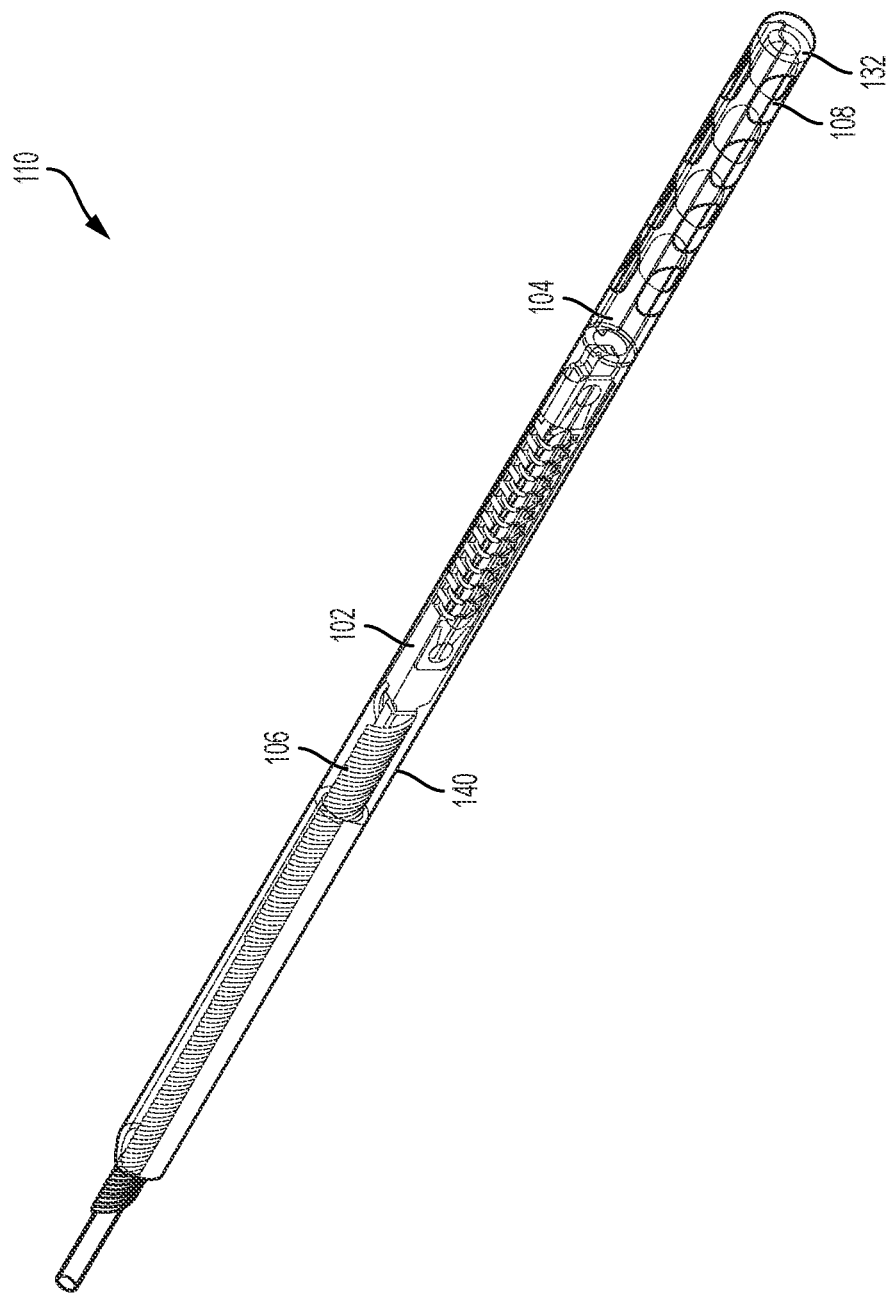
FIG. 3 illustrates a perspective view of the distal end of the stimulation lead illustrated in FIG. 2.

FIG. 3 illustrates a perspective view of the distal end 110 of the stimulation lead 100. As an overview, the distal end 110 includes a microelectrode film 104 with a plurality of electrodes 108. The microelectrode film 104 is coupled with a support tube 132. The distal end 110 also includes the support comb 102. The support comb 102 can enable the attachment of the wires 106 to the microelectrode film 104. The distal end 110 also includes a probe shaft 140. Components of the distal end 110 are described below in connection to FIGS. 4-9, among others, and the assembled distal end 110 is further described in connection to FIGS. 10-17, among others.

Figure 4:
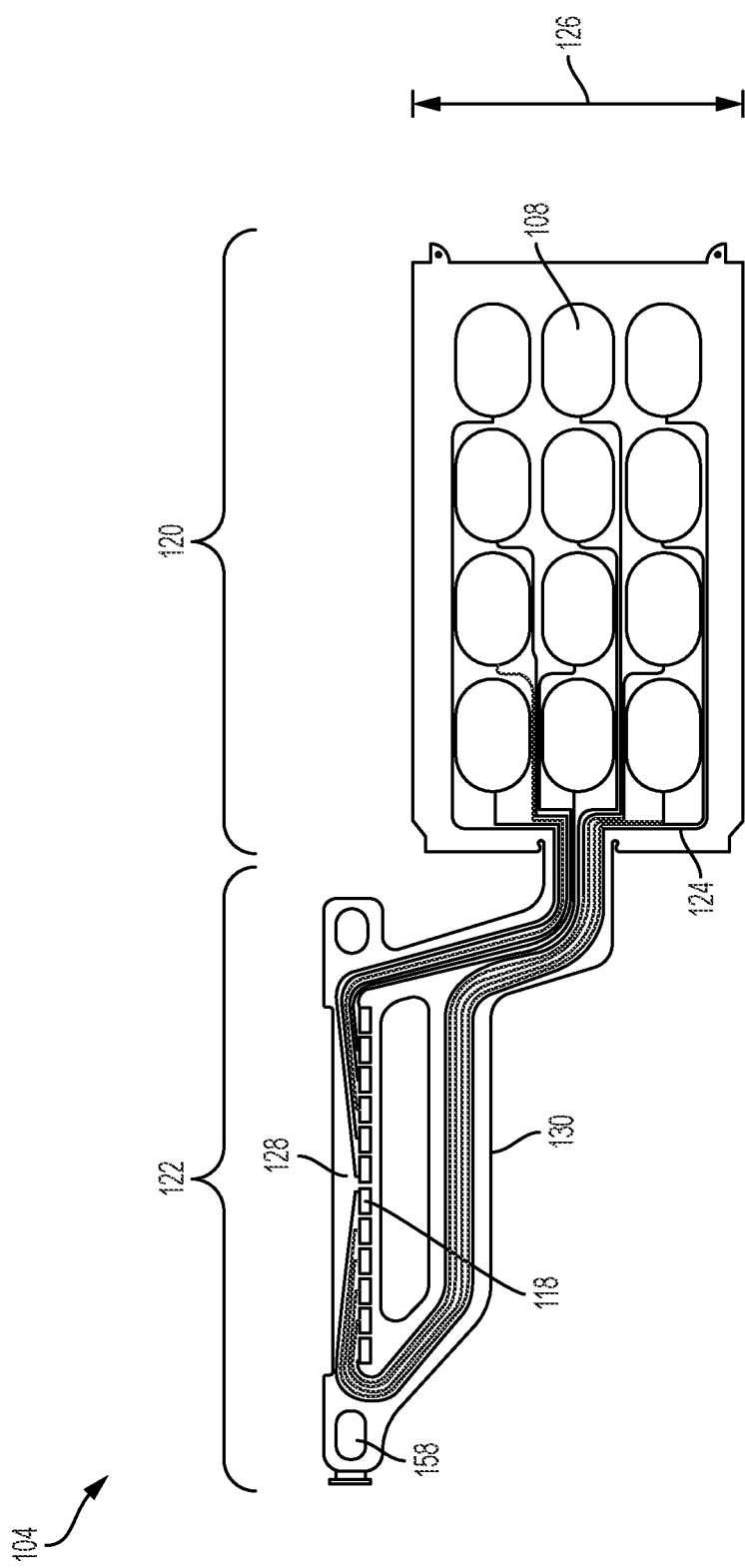
FIG. 4 illustrates a top view of the microelectrode film for use in the stimulation lead illustrated in FIG. 2.

The distal end 110 includes a microelectrode film 104. FIG. 4 illustrates a top view of the microelectrode film 104. FIG. 4 illustrates the microelectrode film 104 in a planar configuration. The microelectrode film 104 includes a body 120 and an extension 122. The body 120 includes a plurality of electrodes 108. The extension 122 includes a plurality of contacts 118. The contacts 118 can be coupled with the electrodes 108 via traces 124.

Figure 5:
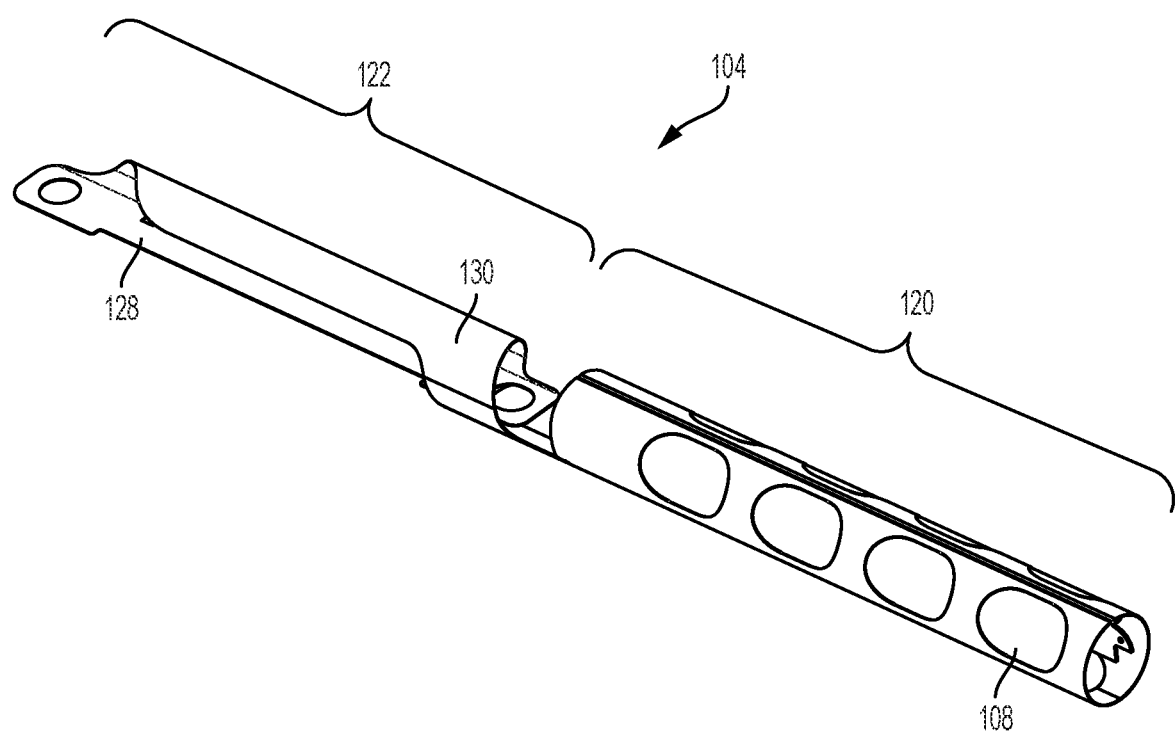
FIG. 5 illustrates the microelectrode film in a rolled configuration.

The microelectrode film 104 includes the body 120. The body 120 can include a plurality of electrodes 108. The body 120 can include between about 4 and about 64, between about 8 and about 32, between about 8 and about 24, or between about 4 and about 12 electrodes 108. The electrodes 108 can be configured as directional or omnidirectional electrodes. For example, in an omnidirectional configuration, the electrode 108 can extend substantially the height 126 of the body 120, such that the electrode 108 wraps substantially around (e.g., at least 80%, or at least 90%) the circumference of the distal end 110 when the microelectrode film 104 is formed into a cylinder (as illustrated in FIG. 5). In a directional configuration, as illustrated in FIG. 4, the electrodes 108 only extend a portion of the height 126 of the microelectrode film 104. For example, in a directional configuration the electrodes 108 may each only extend between about 10% and about 80%, between about 10% and about 60%, between about 10% and about 40%, or between about 10% and about 25% of the height 126 of the body 120. The electrodes 108 can be grouped in column to span the height 126. One or more of the directionally configured electrodes 108 can be electrically coupled together to form an omnidirectional electrode 108. The coupling between at least two directionally configured electrodes 108 to form an omnidirectional electrode 108 can occur electrically by connecting two traces 124 within microelectrode film 104 or by connecting terminal contacts 116 via the wires 106.

The microelectrode film 104 can include a plurality of traces 124. The traces 124 can couple the electrodes 108 with one or more contacts 118. The microelectrode film 104 can include the same number of contacts 118 and electrodes 108 such that each electrode 108 is coupled with a single contact 118. The microelectrode film 104 can include fewer contacts 118 than electrodes 108, such that more than one electrode 108 is coupled with the same contact 118 (to form, for example, an omnidirectional electrode). Each trace 124 can make one or more connections with an electrode 108. For example, a trace 124 can branch into two or more periphery traces that couple with the electrode 108 at couple with the electrode 108 at several points around the periphery of the electrode 108. Making multiple connections with each of the electrodes 108 can increase the reliability of the microelectrode film 104.

The extension 122 can include the contacts 118. The contacts 118 can provide an interface where the wires 106 are coupled with the microelectrode film 104. For example, each of the wire 106 can be wire bonded or laser bonded with a respective one of the contacts 118.

The extension 122 can include a first leg 128 and a second leg 130. The contacts 118 can be disposed on a first face of the first leg 128. The first leg 128 can also include an opening 158 disposed toward each end of the first leg 128. The openings 158 can be holes through the first leg 128. The openings 158 can align with inlets that are formed in the attachment face of the support comb 102 (and described further below in relation to FIG. 8, among others). The second leg 130 can include a subset of the traces 124 that run from the contacts 118 to the electrodes 108. Running the subset of the traces 124 along the second leg 130 can enable a greater number of traces 124 (and therefore electrodes 108) to be incorporated into the microelectrode film 104 when compared to a system that routes the traces 124 along a single leg.

FIG. 5 illustrates the microelectrode film 104 in the rolled configuration. As illustrated, opposite edges of the body 120 are rolled toward one another to form a cylinder. The second leg 130 is rolled about the first leg 128 to form a second portion of the cylinder. As described in relation to FIGS. 5 and 6, among others, the body 120 can be rolled about a support tube.

Figure 6:
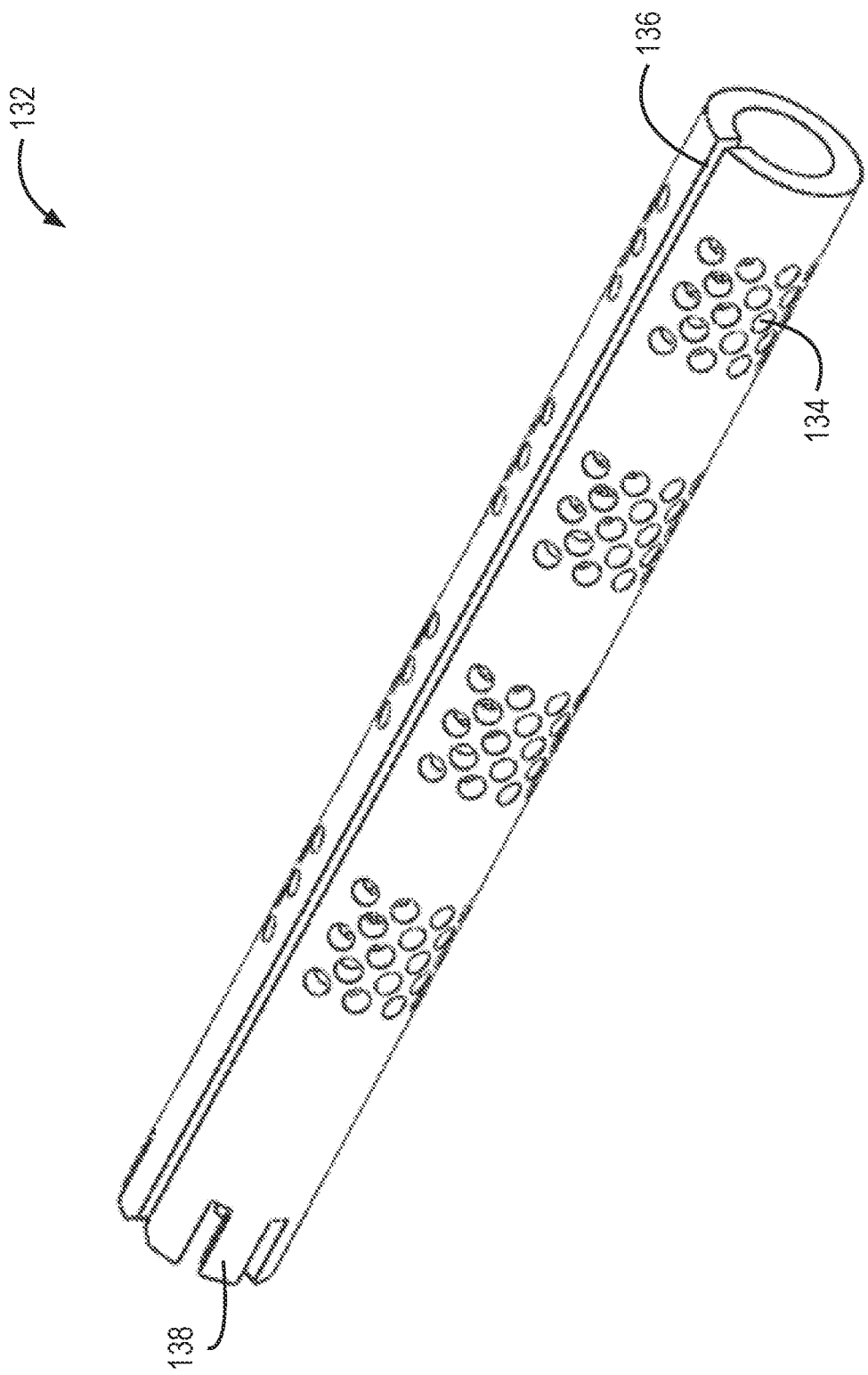
FIG. 6 illustrates an example support tube for use in the stimulation lead illustrated in FIG. 2.

FIG. 6 illustrates an example support tube 132. The support tube 132 can include a plurality of markers 134. The support tube 132 can include a slot 136. The proximal end of the support tube 132 can include a plurality of merlons 138.

The support tube 132 can include a radio opaque metal, such as a medical grade stainless steel, non-metal materials, such as plastic, or a combination thereof. The support tube 132 can include a plurality of markers 134. The markers 134 can be radio opaque. For example, the markers 134 can be visible when the stimulation lead 100 is imaged with a CT scanner or x-ray. When the support tube 132 is manufactured from a radio opaque metal, the markers 134 can be holes or voids in the body of the support tube 132. The markers 134 can pass through the wall of the support tube 132. When the markers 134 are holes through the wall of the support tube 132, the regions without the markers 134 can be relatively more radio opaque when compared to the portions of the support tube 132 with the markers 134. The electrodes 108 can be aligned with the markers 134. The electrodes 108 can be aligned with the regions between the markers 134. The support tube 132 can be manufactured in a plastic material and the markers 134 can be made radio opaque by either, a localized doping of the polymer such as Boron bombardment or by backfilling with a doped polymer for example Boron doped plastic.

The support tube 132 can include a plurality of merlons 138. The merlons 138 can be a plurality of extensions that extend from one end of the support tube 132. Each merlon 138 can be separated from a neighboring merlon 138 by a gap or crenel. Each of the merlons 138 can be about between about 0.2 mm and about 2 mm, between about 0.4 mm and about 1.5 mm, between about 0.2 mm and about 1 mm, or between about 0.4 mm and about 0.6 mm long. The merlons 138 can have a circumferential pitch of about 0.1 mm to about 2 mm, between about 0.1 mm and about 1.5 mm, between about 0.1 mm and about 1 mm, between about 0.1 mm and about 0.5 mm, or between about 0.2 mm and about 4 mm.

The merlons 138 are configured to mate with the support comb 102. The merlons 138 are configured to mate with the probe shaft of the stimulation lead 100. The probe shaft can be formed by an epoxy over-molding process. The merlons 138 can provide groves and ridged to into which the epoxy can flow and bond to form the probe shaft.

The support tube 132 can include a slot 136. The slot 136 can run the length of the support tube 132. The slot 136 can pass through the wall of the support tube 132 or can form a channel in the outer face of the support tube 132.

Figure 7:
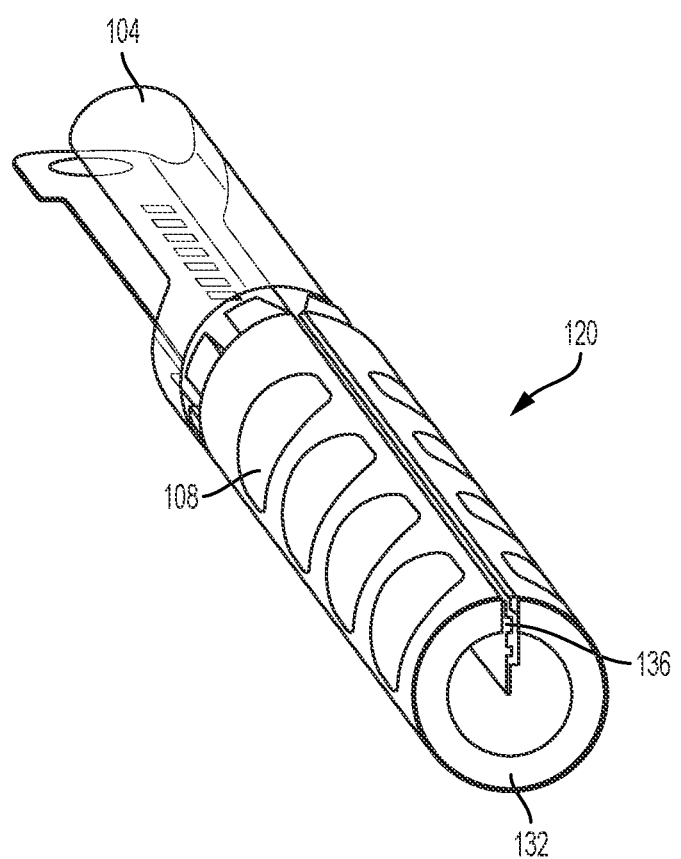
FIG. 7 illustrates the microelectrode film coupled with the support tube, as viewed from the distal end of the support tube.

FIG. 7 illustrates the microelectrode film 104 coupled with the support tube 132, as viewed from the distal end of the support tube 132. A first face of the body 120, which includes the electrodes 108 can faces outward and away from the support tube 132. A second face of the microelectrode film's body 120 is coupled with the external face of the support tube 132 to form a cylinder. The opposing edges of the body 120 are inserted through the slot 136.

Figure 8:
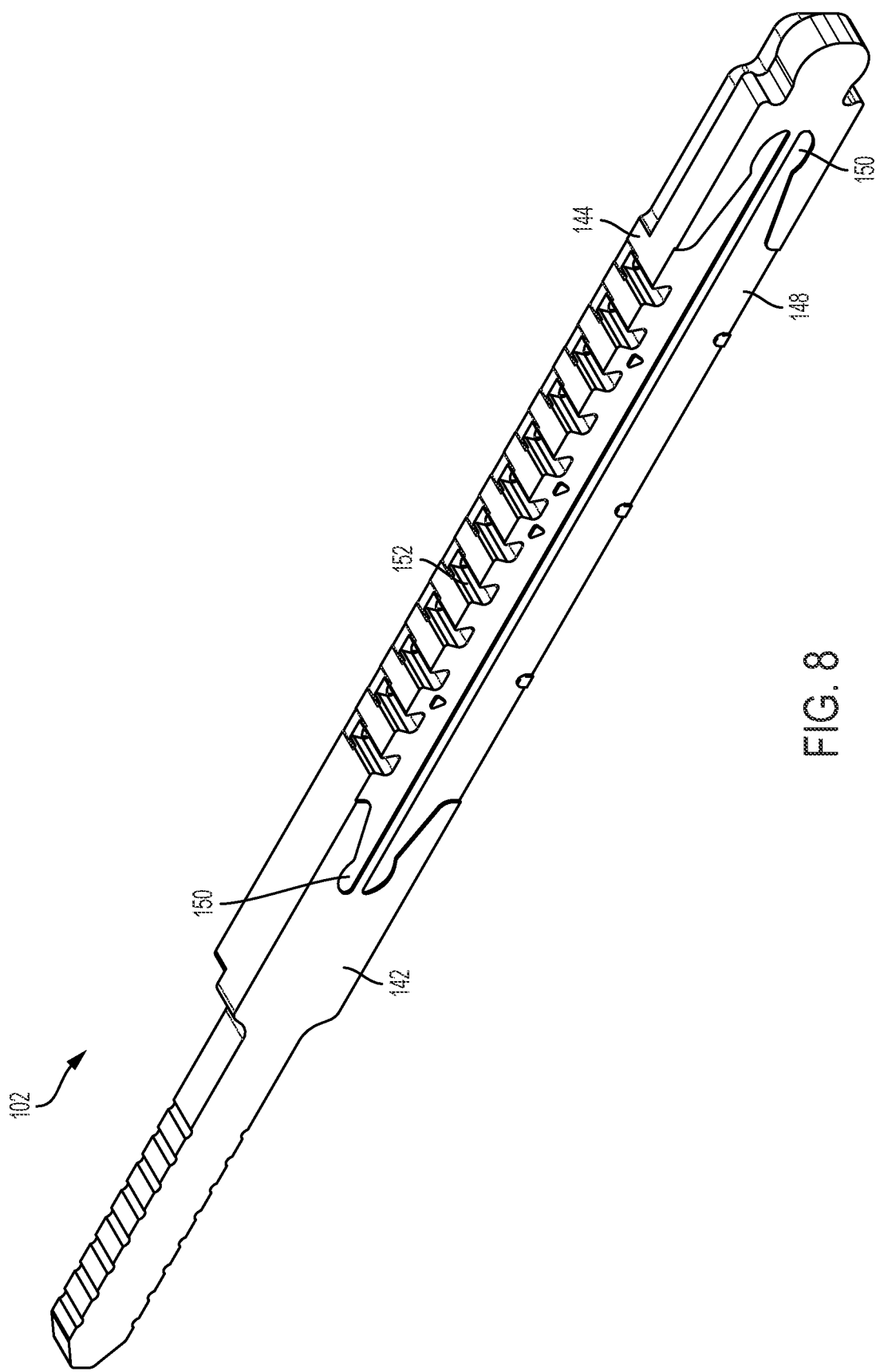
FIGS. 8-10 illustrate an example support comb for use in the stimulation lead illustrated in FIG. 2.

FIG. 8 illustrates an attachment face of the support comb 102 and a first routing face 144 of the support comb 102. The attachment face 142 includes a channel 148. The attachment face 142 of the support comb 102 is configured to couple with a face of the microelectrode film 104. The channel 148 is configured to route an adhesive under a portion of face of the microelectrode film 104 that is coupled with the attachment face 142. The channel 148 can be between about 5 µm and about 40 µm, between about 10 µm and about 30 µm, or between about 10 µm and about 20 µm. During the manufacturing of the stimulation lead 100, a face of the microelectrode film 104 can be coupled with the attachment face 142 of the support comb 102 through a mechanical means, such as a clamp. The inlets 150 can extend past the portion of the microelectrode film 104 that is coupled with the attachment face 142. An adhesive can be added to the inlets 150. Capillary action can transport the adhesive along the length of the channel 148 and under the face of the microelectrode film 104 that is coupled with the attachment face 142. Once the adhesive sets, the mechanical means for holding the microelectrode film 104 against the attachment face 142 can be released.

The support comb 102 can include a first routing face 144. The first routing face 144 can include plurality of slots 152 (which can also be referred to as channels 152). The first routing face 144 can include a slot 152 for each of the wires 106. During the manufacturing process, each of the contacts 118 can be substantially aligned with one of the slots 152 to facilitate coupling the wires 106 with contacts 118. For example, each of the wires 106 can pass through a respective slot 152 to align with a different contact 118. The pitch of the slots 152 can match the pitch of the contacts 118.

Figure 9:
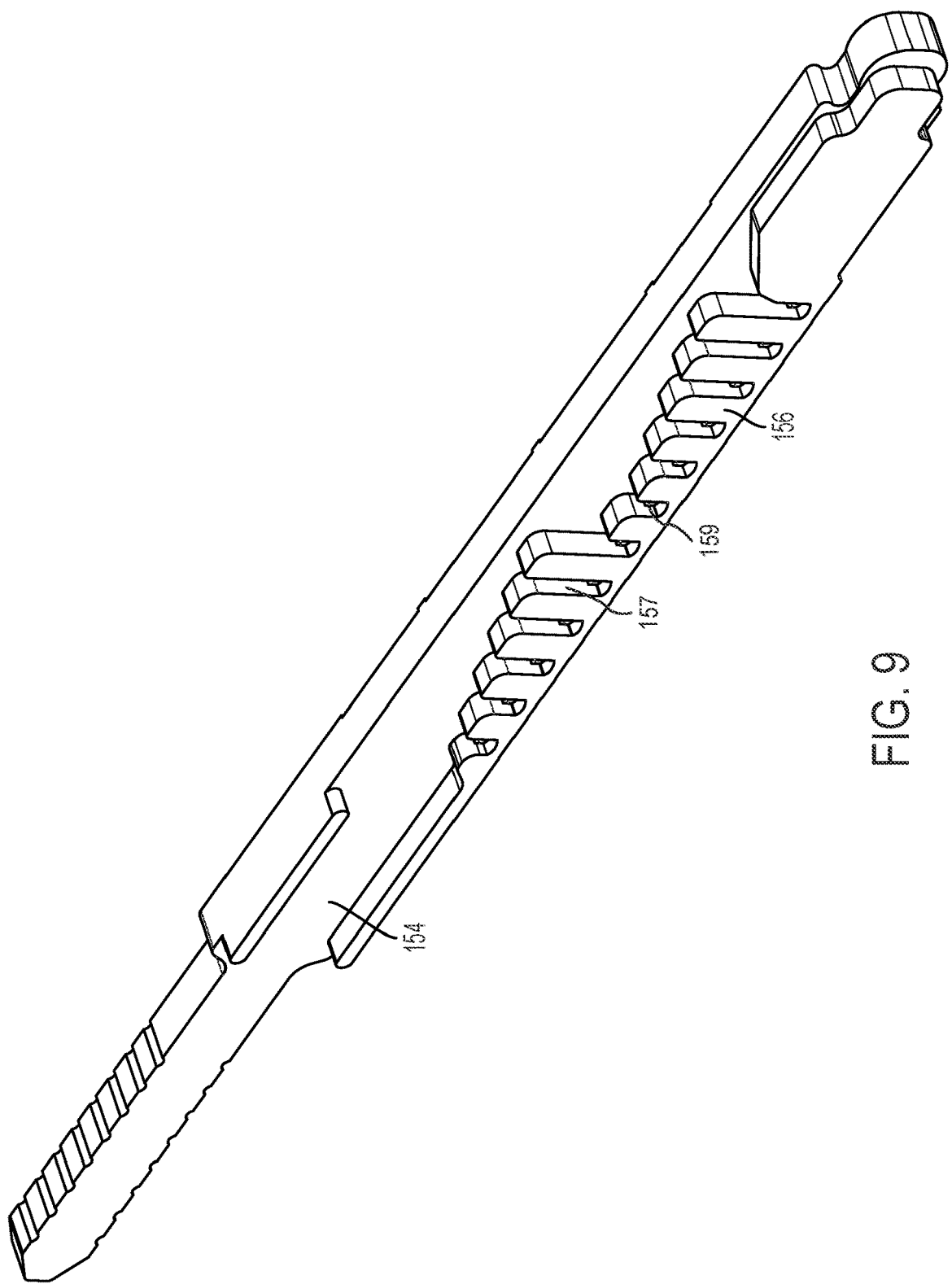

FIG. 9 illustrates a second routing face 154 of the support comb 102. The second routing face 154 is opposite the attachment face 142. The second routing face 154 can include a plurality of fingers 156. The fingers 156 are raised protrusions that can form channels 157 in the second routing face 154. Each of the channels 157 can terminate in a hole 159 that passed to the slots 152 on the first routing face 144.

Figure 10:
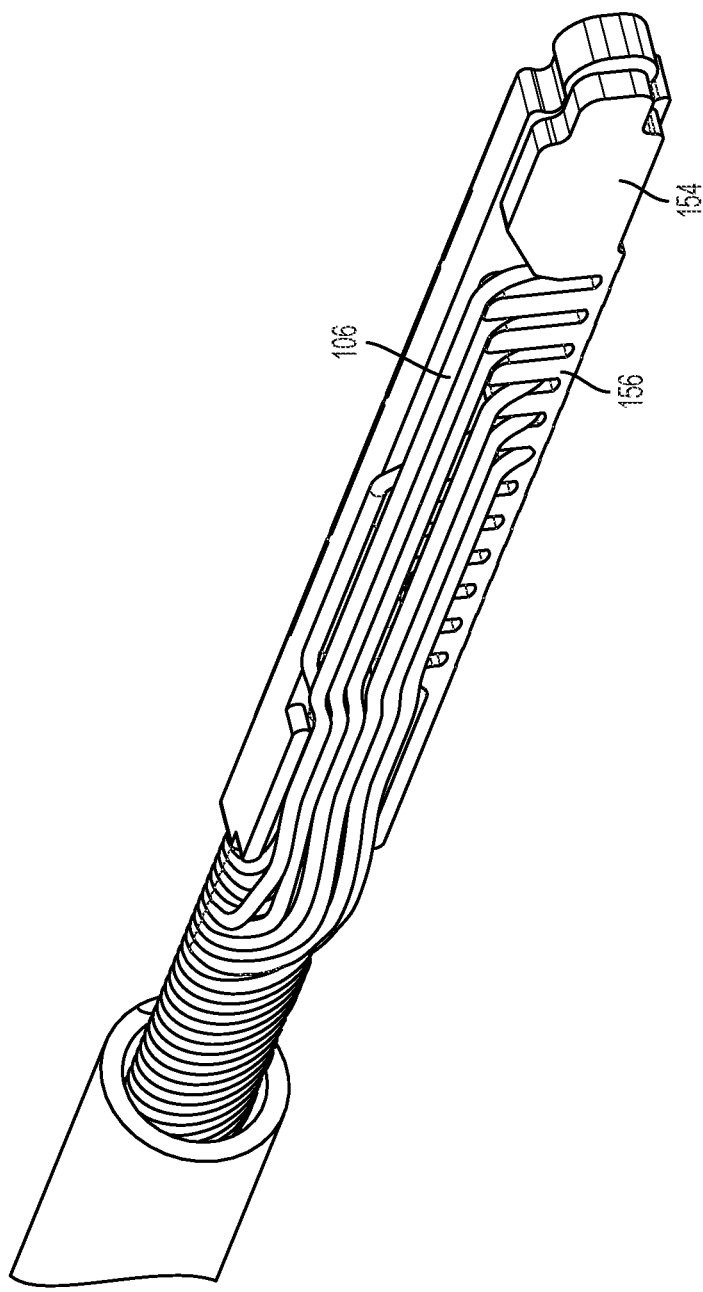
Figure 11:
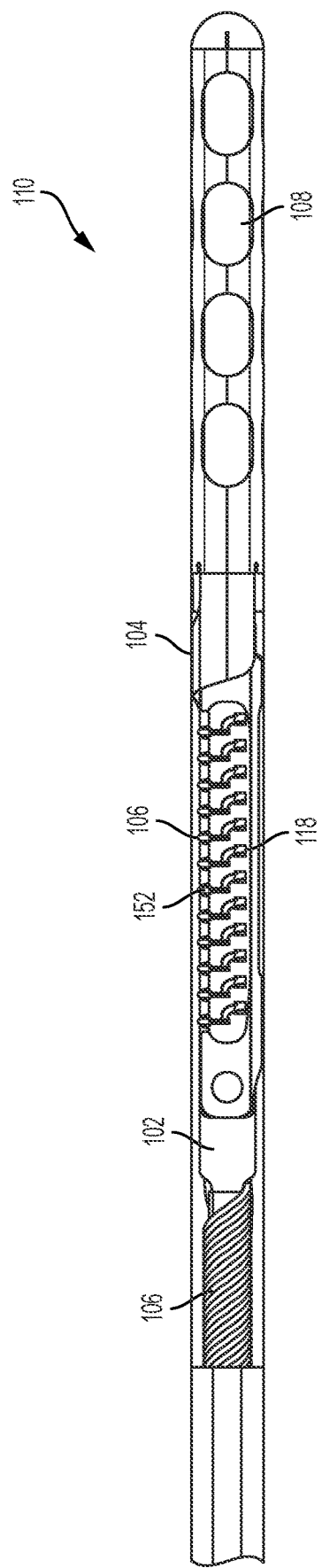
FIGS. 11-14 illustrate views of the distal end of the stimulation lead illustrated in FIG. 2.
Figure 12:
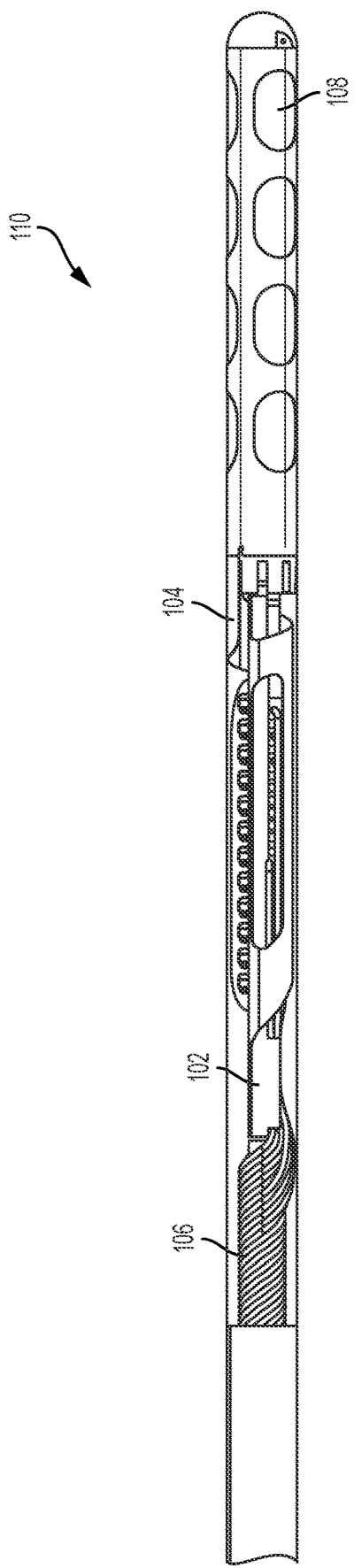
Figure 13:
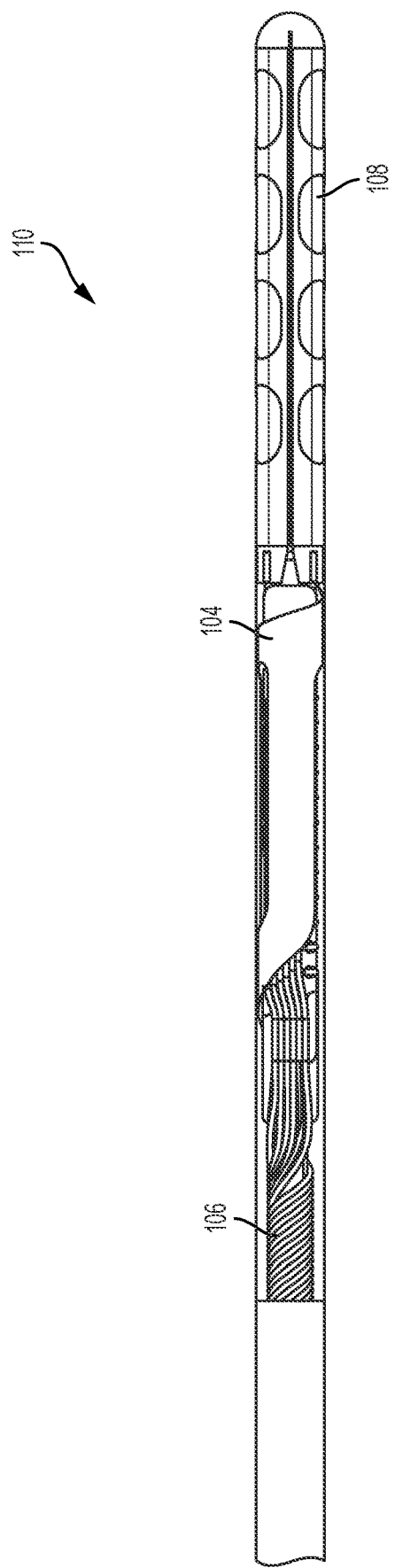
Figure 14:
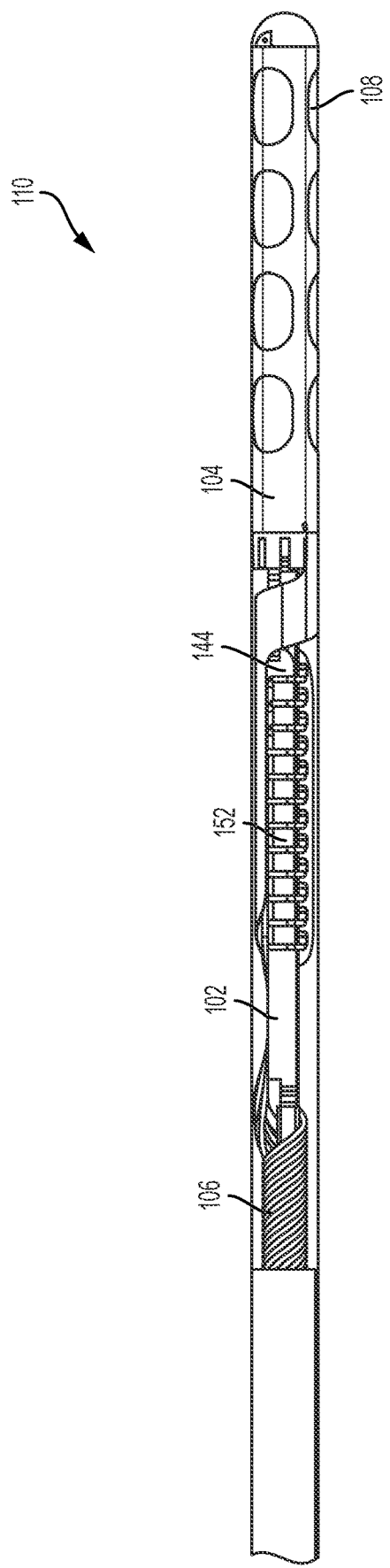

FIG. 10 illustrates the second routing face 154 with wires 106 passing along the second routing face 154. The wires 106 can pass into the channels 157 defined by the fingers 156. From the channels 157, the wires 106 can pass through the hole 159 at the end of the channel 157 and into one of the respective slots 152 on the first routing face 144. The color coding of the wires 106 can enable the appropriate routing of wires 106 from each one of the terminal contacts 116 to the corresponding electrodes 108 of the distal end 110.

FIGS. 11-14 illustrate different face views of the distal end 110. Each of the views illustrated in FIGS. 11-14 illustrate a view of the distal end 110 of the stimulation lead 100 rotated 90 degrees with respect to the previous FIG. For example, FIG. 11 can be said to illustrate a top view of the distal end 110, FIG. 12 can be said to illustrate a first side view of the distal end 110, FIG. 13 can be said to illustrate a bottom view of the distal end 110, and FIG. 14 can be said to illustrate a second side view of the distal end 110. The preceding "top", "first side," "second side," and "bottom" are provided for reference only as any face of the distal end 110 can serve as the "top," "bottom," etc. For example, the placement of the electrodes 108 around the circumference of the distal end 110 enable any face (or angle) of the distal end 110 to serve as the top, bottom, or side of the distal end 110.

Referring to FIGS. 11-14 together, among others, the distal end 110 includes the microelectrode film 104. The microelectrode film 104 includes a plurality of electrodes 108. The electrodes 108 are coupled with the terminal contacts 116 via the wires 106. The distal end 110 also includes the support comb 102. The support comb 102 can facilitate the management of the wires 106 within the shaft of the distal end 110. The support comb 102 can also secure or hold the terminating ends of the wires 106 near the contacts of the microelectrode film 104. Positing the terminating ends of the wires 106 near the contacts of the microelectrode film 104 can enable for improved efficiencies in manufacturing as the support comb 102 can provide alignment between the wires 106 and the contacts 118 of the microelectrode film 104.

Figure 15:
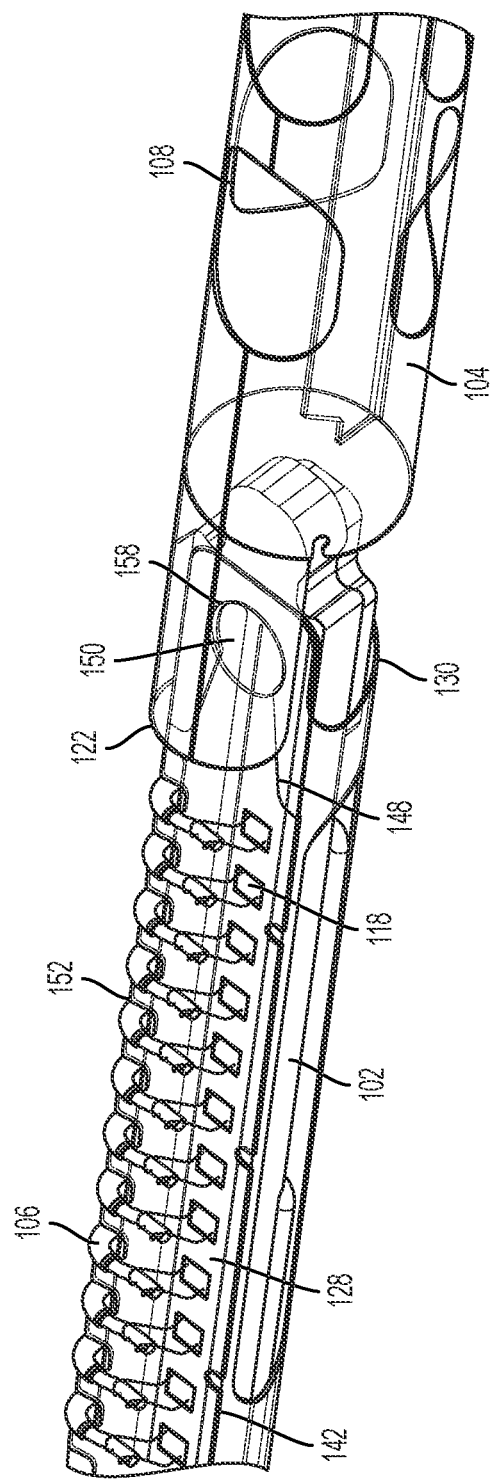
FIG. 15 illustrates a partial view of the interface between the support comb and the microelectrode film in the stimulation lead illustrated in FIG. 2.

FIG. 15 illustrates an enlarged view of the interface between the support comb 102 and the microelectrode film 104. FIG. 15 illustrates the microelectrode film 104 in the rolled or cylindrical configuration. The extension 122 of the microelectrode film 104 is rolled around the support comb 102 such that support comb 102 is positioned within a lumen defined by the rolled (or cylindrical) microelectrode film 104. The second leg 130 is wrapped around the support comb 102 and positioned toward the support comb's second routing face 154 (illustrated in FIG. 15 as the backside of the support comb 102). The first leg 128 can be coupled with the attachment face 142.

The first leg 128 of the microelectrode film 104 can be coupled with the attachment face 142. The first leg 128 can include a first face that includes the contacts 118 and a second face, opposite the first face, that can couple with the support comb 102. The second face can be coupled with the attachment face 142. The first leg 128 can be positioned on the attachment face 142 such that the opening 158 substantially aligns with the inlet 150. For example, before rolling the extension 122 around the support comb 102, an adhesive can be delivered to the inlet 150 through the opening 158 in the first leg 128. Through capillary action, the adhesive can flow through the channel 148 and under the first leg 128 to couples the first leg 128 (e.g., the second face of the first leg 128) with the attachment face 142.

Coupling the first leg 128 with the attachment face 142, the contacts 118 can be substantially aligned with the slots 152. The contacts 118 can be offset from the slots 152. For example, each of the contacts 118 can be positioned between neighboring slots 152. The slots 152 can enable wire management and position the wires 106 in a correct position for bonding with the contacts 118. For example, the wires 106 can pass through each of the slots 152 to align with one of the contacts 118. The wires 106 can be coupled with the contacts 118. The wires 106 can be wire bonded or welded with the contacts 118.

Figure 16:
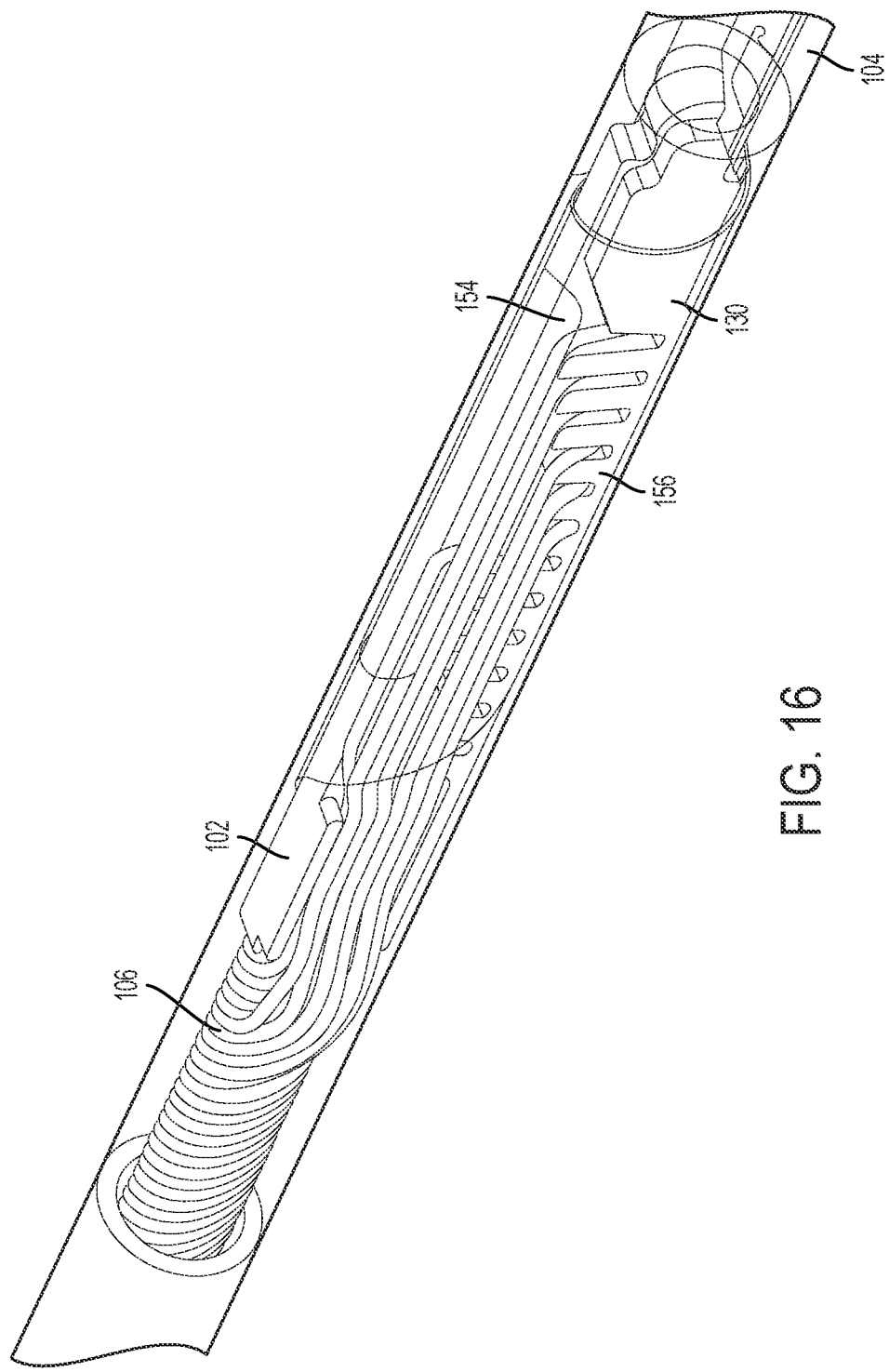
FIG. 16 illustrates a partial view of an example support comb that can be used in the stimulation lead illustrated in FIG. 2.

FIG. 16 illustrates an enlarged view of the support comb 102. FIG. 16 substantially illustrates the back side of the support comb 102 (and distal end 110) with respect to FIG. 15.

As illustrated, the second leg 130 of the microelectrode film 104 is rolled around the support comb 102. The wires 106 pass along the second routing face 154 of the support comb 102. Each of the wires 106 pass through a channel formed by the fingers 156. The wires 106 can pass through a hole 159 formed at the end of the channel 157 and into the slots 152. The fingers 156 (and the channels formed thereby) can enable routing of the wires 106 along the support comb 102 and to the slots 152 where the wires 106 can be coupled with the contacts 118.

Figure 17:
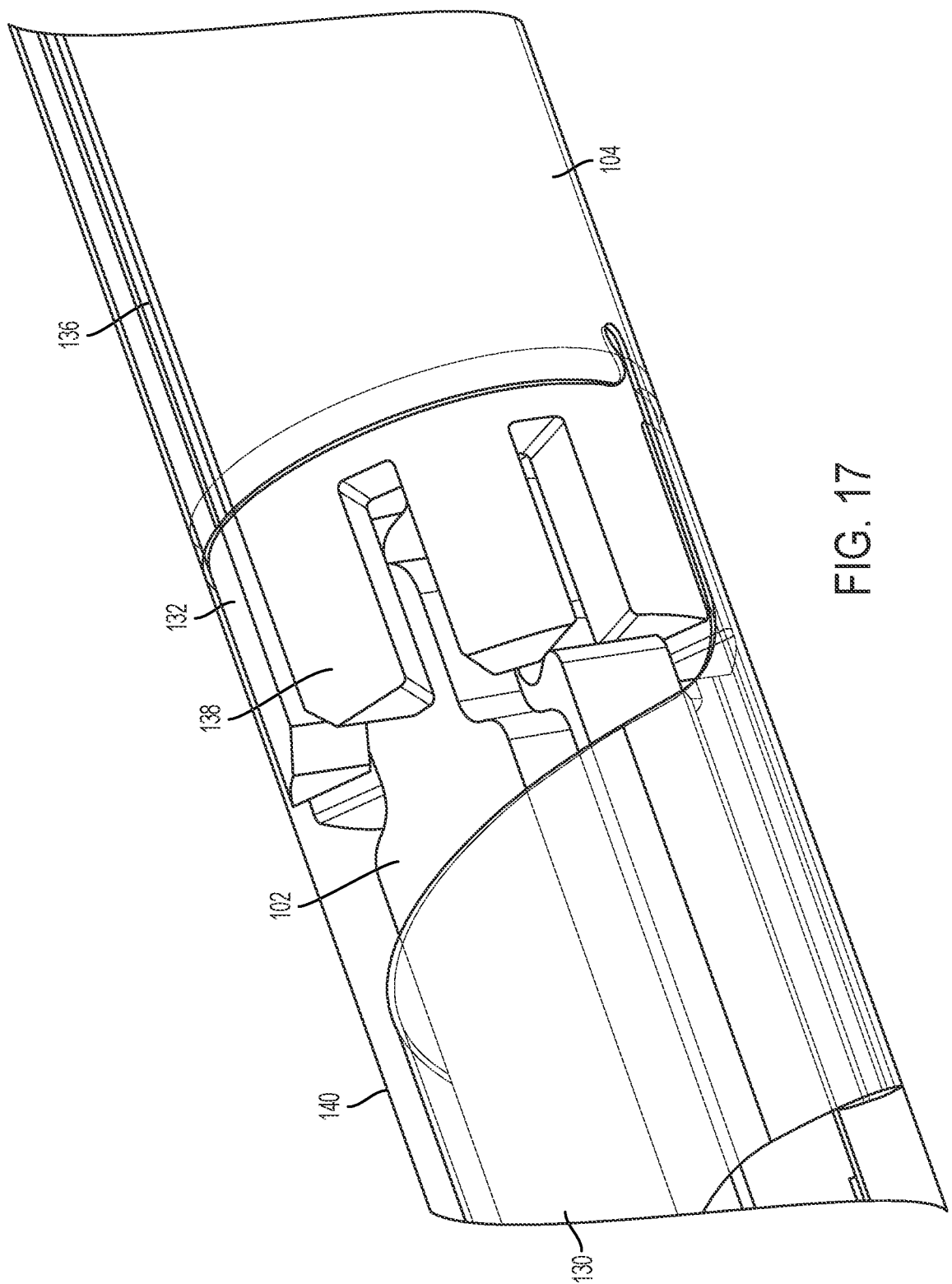
FIG. 17 illustrates a partial view of the coupling of the support comb with the support tube.

FIG. 17 illustrates an enlarged view of the coupling of the support comb 102 with the support tube 132. A first end of the support comb 102 can include a knob or other structure that is configured to fit within a portion of the support tube 132. The merlons 138 can surround the knob at the first end of the support comb 102. The probe shaft 140 can be formed through an epoxy over molding process. The epoxy can flow into the areas between the merlons 138 to form a probe shaft 140 that is coupled with the support tube 132. The epoxy of the probe shaft 140 can encase the support comb 102 and the second leg 130 within the body of stimulation lead's distal end 110. The probe shaft 140 can be formed from an injection molding or micromachining process.

Figure 18:
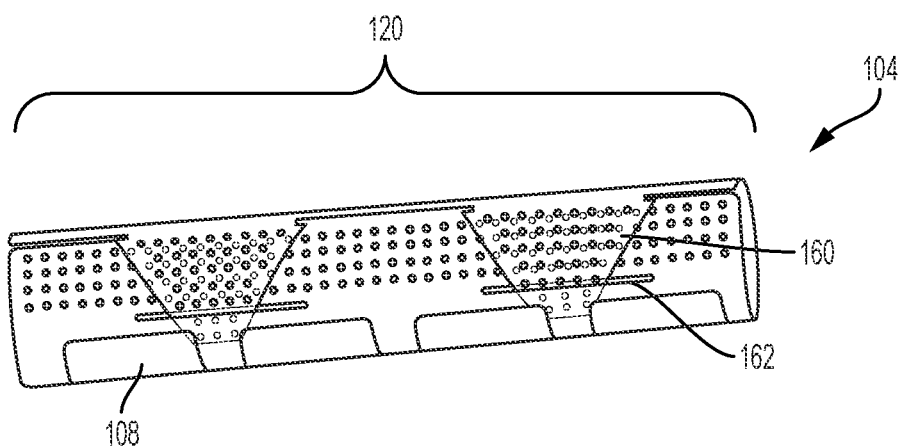
FIGS. 18 and 19 illustrate example configurations of the microelectrode film with tabs.
Figure 19:
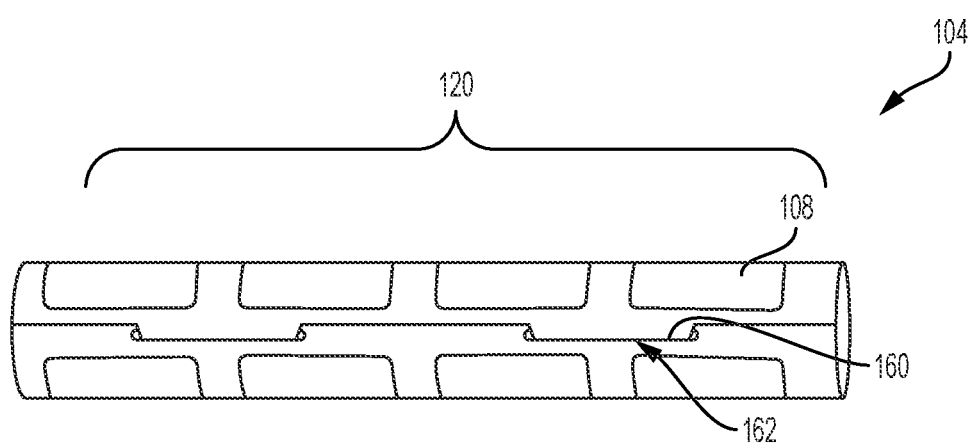

FIGS. 18 and 19 illustrate an example configuration of the microelectrode film 104 and method for forming the microelectrode film 104 into a cylinder. FIG. 19 illustrates the body 120 portion of the microelectrode film 104 in a partially rolled state. A first edge of the body 120 can include a plurality of tabs 160. The opposite edge (or towards the opposite edge) can include a plurality of slots 162. The body 120 can include a slot 162 for each of the tab 160. The tabs 160 can be tapered—narrowing as the tab 160 extends from the body 120. For example, the tabs 160 can be shaped like the head of an arrow. Each of the tabs 160 can slide into a respective one of the slots 162. The tabs 160 can include a barb that locks the tab 160 into the slot 162 once the tab 160 is inserted into the slot 162 past the barb. FIG. 19 illustrates the body 120 with the tabs 160 fully inserted into the slots 162 to form a cylinder.

Figure 20:
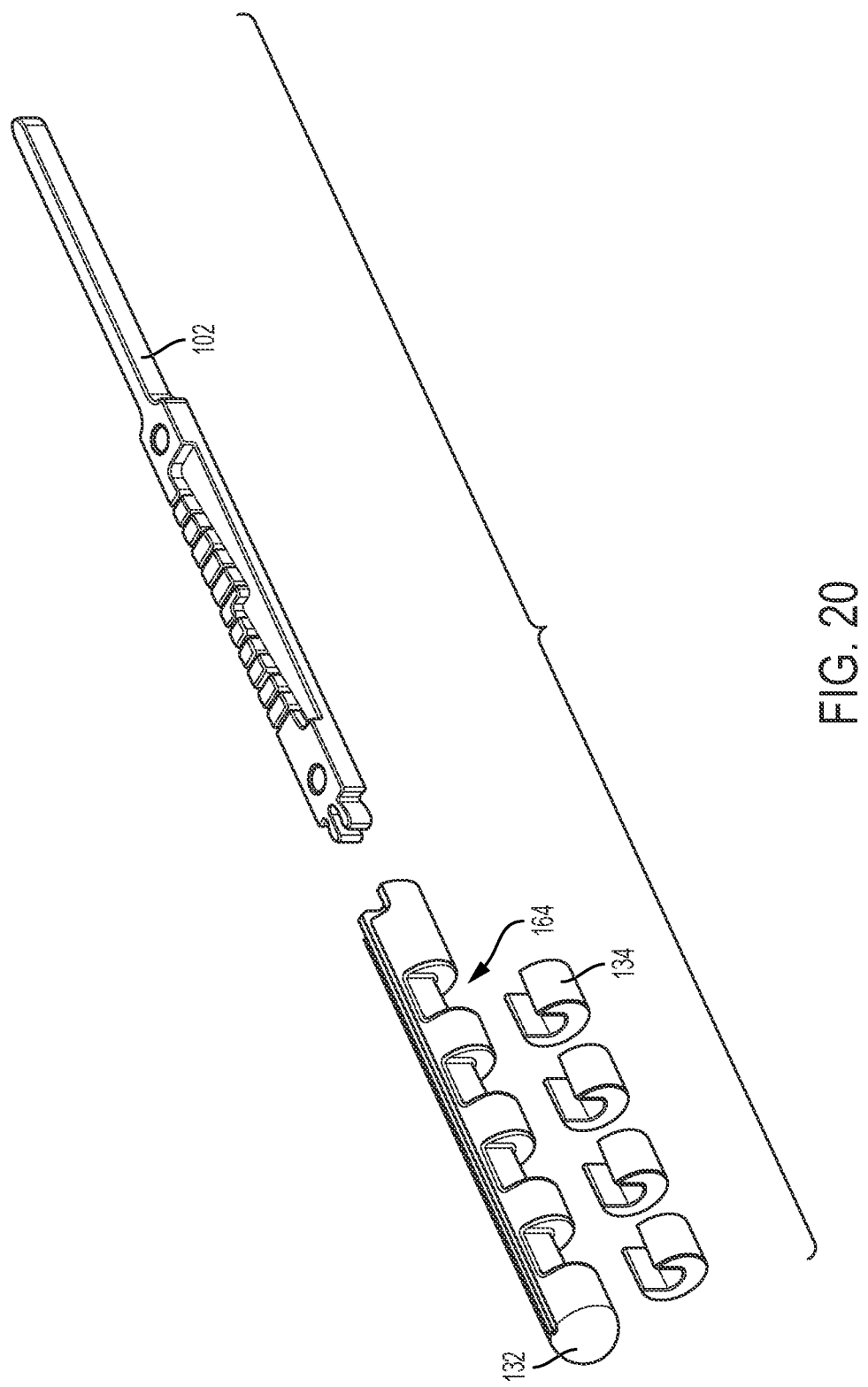
FIG. 20 illustrates an example support tube and markers for use in the system illustrated in FIG. 1.

FIG. 20 illustrates an example support tube 132 and markers 134. The example support tube 132 illustrated in FIG. 20 can be manufactured from a non-magnetic or non-radio opaque material. The markers 134 can be manufactured from a radio opaque material. The support tube 132 can include a plurality of grooves 164. The grooves 164 can be shaped to receive the markers 134. The markers 134 can be secured into the grooves 164 with an adhesive, clip, or pressure fitting. When the microelectrode film 104 is coupled with the support tube 132, the electrodes 108 can be aligned with the markers 134.

Figure 21:
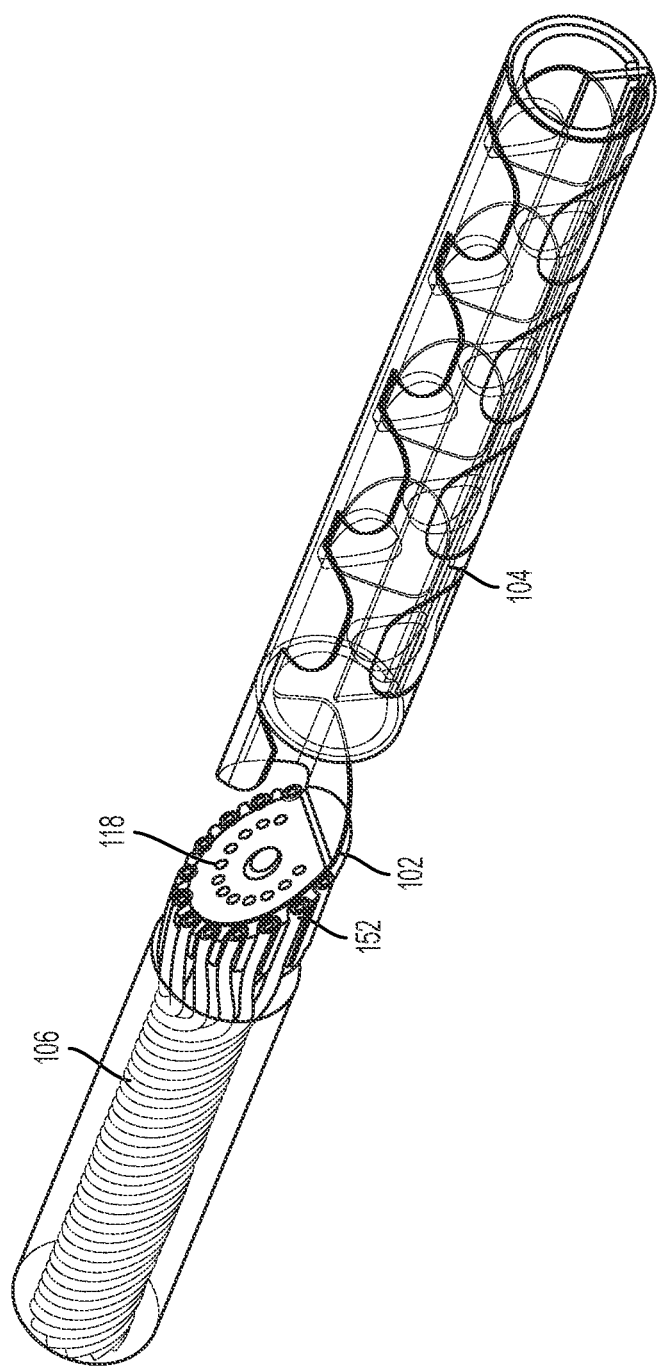
FIG. 21 illustrates an example support comb with a circular configuration for use in the system illustrated in FIG. 1.

FIG. 21 illustrates an example support comb 102 in a circular configuration. The support comb 102 can include a plurality of slots 152 around the circumference of the support comb 102. The extension of the microelectrode film 104 can be disk shaped and can include a plurality of contacts 118 distributed toward the circumference of the extension. The wires 106 can pass through each of the slots 152 toward the contacts 118. The slots 152 can align the wires 106 with the contacts 118. The wires 106 can be wire bonded or welded to the contacts 118.

Figure 22:
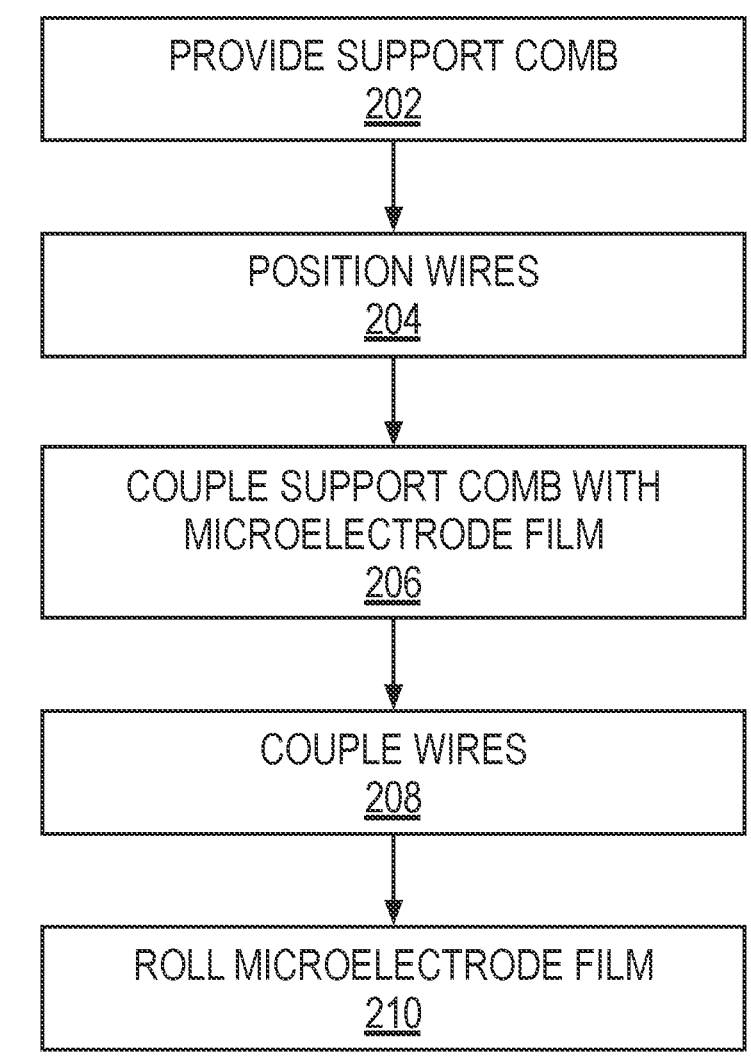
FIG. 22 illustrates an example method to manufacture the lead device for use in the system illustrated in FIG. 1.

FIG. 22 illustrates an example method 200 to manufacture a lead device. The method 200 can include providing a support comb (BLOCK 202). The method 200 can include positioning a plurality of wires (BLOCK 204). The method 200 can include coupling the support comb with a microelectrode film (BLOCK 206). The method 200 can include coupling the wires with the microelectrode film (BLOCK 208). The method 200 can include rolling the microelectrode film (BLOCK 210).

As set forth above, the method 200 can include providing a support comb (BLOCK 202). Referring also to FIGS. 1-21, the support comb 102 can include an attachment face 142 and first routing face 144. The first routing face 144 can include a plurality of slots 152. The microelectrode film 104 can include a second routing face 154. The second routing face 154 can include a plurality of fingers 156 that form channels on the second routing face 154. The channels 157 can terminate in a hole 159 that connects the channels 157 of the second routing face 154 with the slots 152 of the first routing face 144. The attachment face 142 can include a channel 148.

The support comb 102 can be manufactured by an injection molding process, a micro-machining process, a photolithography process, or 3D-printing process. The support comb 102 can be manufactured from silicon, plastic, metal, liquid crystal polymers (LCP), or other material. Radio opaque materials can include included into the support comb 102 to enable the distal end 110 to be visualized during an X-ray. For example, the polymers used in an injection molding process can be doped with a radio opaque material such as Barium Sulfate (BaSO4), Boron, or metal rings, bands, or components can be incorporated into the support comb 102.

The method 200 can include positioning the wires (BLOCK 204). Referring to FIG. 10, among others, the wires 106 can uncoil and run along the second routing face 154. The second routing face 154 can arrange the wires 106. The second routing face 154 can include a plurality of fingers 156 that can define channels 157. A wire 106 can pass through a respective channel 157 and through a hole 159 at the end of the channel 157 that couples the channel 157 with a slot 152. Each of the wires 106 can pass through a respective one of the slots 152. The slots 152 can hold and position the wires 106. For example, the slots 152 can hold each of the wires 106 in a fixed proximity to a respective contact 118.

The method 200 can include coupling the support comb 102 with a microelectrode film 104 (BLOCK 206). The microelectrode film 104 can include different portions. For example, the microelectrode film 104 can include a body 120 and an extension 122. The body 120 can include a plurality of electrodes 108. The extension 122 can include a plurality of legs. One of the legs can include a plurality of contacts 118. Both the extension 122 and the body 120 can include a plurality of traces 124.

The microelectrode film 104 can include a stack of insulating and conducting layers. The microelectrode film can be a thin-film, microelectromechanical systems (MEMS) electrode film. The conducting layers can include the traces 124, the contacts 118, and the electrodes 108. The different conducting layers can be isolated from one another by the insulating layers. The insulating layers can also isolate the conducting layers (or portions thereof) from the external environment. The microelectrode film 104 can be manufactured as a planar film using additive manufacturing processes.

The microelectrode film 104 can be coupled with the support comb 102 by coupling a first portion of the microelectrode film 104 with the attachment face 142. For example, a portion of the extension 122 can be coupled with the attachment face 142. The first leg 128 of the extension 122, which can include a plurality of contacts 118 can be coupled with the attachment face 142. The face opposite the face with the contacts 118 can be coupled with the attachment face 142 such that the contacts 118 faces away from the support comb 102.

When coupling the microelectrode film 104 with the support comb 102, the openings 158 of the extension 122 can be aligned with the inlets 150 of the support comb 102. The microelectrode film 104 can be coupled with the support comb 102 by applying an adhesive to the inlets 150. Capillary force can drive the adhesive from the inlets 150 and through the channel 148 to underfill the space between the microelectrode film 104 and the support comb 102 formed by the channel 148. Once cured, the adhesive can couple the microelectrode film 104 with the support comb 102.

The method 200 can include coupling the wires with the microelectrode film (BLOCK 208). Also, Referring to FIG. 15, among others, the wires 106 can pass through a respective channel on the second routing face 154 and into a respective slot 152. The slot 152 can position each of the wires 106 near one of the contacts 118. The wires 106 can be coupled with the contacts 118 with wire bonding, welding, or laser bonding.

The method 200 can include rolling the microelectrode film (BLOCK 210). The extension 122 of the microelectrode film 104 can be rolled about the support comb 102. The body 120 of the microelectrode film 104 can be rolled about the support comb 102. Rolling the extension 122 about the support comb 102 can place the second leg 130 of the extension 122 near the second routing face 154 of the support comb 102.

The body 120 of the microelectrode film 104 can be rolled about the support tube 132. The microelectrode film 104 can be coupled with the outer face of the support tube 132. The support tube 132 can include a slot 136. Opposite edges of the body 120 can be inserted into the slot 136.

Once the microelectrode film 104 is rolled, the microelectrode film 104 and support comb 102 can be placed in a mold. The mold can be filled with an epoxy. The epoxy over molding can form a probe shaft 140. The probe shaft 140 can encase the extension 122, the support comb 102, and at least a portion of the wires 106. The probe shaft 140 can flow into the merlons 138 and couples with the support tube 132.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A stimulation lead device, comprising:
 a microelectrode film, the microelectrode film including an extension;
 a support comb, the support comb including:
  an attachment face to couple with the extension of the microelectrode film;
  a slot to receive a wire; and
  a first finger and a second finger that define a channel, the channel to receive the wire.

2. The stimulation lead device of claim 1, comprising:
 the attachment face including a channel, wherein adhesive disposed in the channel couples the support comb with the microelectrode film.

3. The stimulation lead device of claim 1, comprising:
 a support tube coupled with the microelectrode film, the support tube including at least one of a marker and a merlon.

4. The stimulation lead device of claim 1, wherein the extension of the microelectrode film comprises:
 a first leg, the first leg having an electrical contact coupled with an electrode; and
 a second leg, the second leg coupled with the attachment face of the support comb.

5. The stimulation lead device of claim 1, wherein the microelectrode film comprises:
 a first leg and a second leg, the first leg and the second leg rolled around at least a portion of the support comb.

6. The stimulation lead device of claim 1, comprising:
 the support comb disposed at least partially within a volume defined by the extension of the microelectrode film.

7. The stimulation lead device of claim 1, comprising:
 the support comb at least partially coupled with the extension of the microelectrode film.

8. The stimulation lead device of claim 1, comprising:
 the support comb including a routing face, the routing face including the slot to receive the wire.

9. The stimulation lead device of claim 1, wherein the slot aligns the wire with a contact.

10. The stimulation lead device of claim 1, comprising:
 the support comb including a routing face, the routing face including the first finger and the second finger, wherein the second finger is longer than the first finger.

11. The stimulation lead device of claim 1, comprising:
 the support comb including an inlet, the inlet including an adhesive to couple the support comb with the microelectrode film.

12. The stimulation lead device of claim 1, comprising:
 a probe shaft that encases at least a portion of the extension of the microelectrode film, the probe shaft including epoxy.

13. The stimulation lead device of claim 1, comprising:
 the microelectrode film and the support comb disposed at a distal end of the stimulation lead device.

14. The stimulation lead device of claim 1, wherein the extension of the microelectrode film comprises:
 a trace to couple an electrode with a contact.

15. The stimulation lead device of claim 1, wherein the microelectrode film comprises:
 a body having an tab and a slot, the tab of the microelectrode film configured to engage with the slot of the microelectrode film.

16. The stimulation lead device of claim 1, wherein the microelectrode film comprises:
 a body having a plurality of electrodes;
 a plurality of tabs along a first edge of the body;
 a plurality of slots along a second edge of the body, each of the plurality of slots of the microelectrode film to hold a corresponding tab of the plurality of tabs to define a volume at least partially through the body of the microelectrode film.

17. The stimulation lead device of claim 1, comprising:
 the extension of the microelectrode film coupled with the support comb, the extension including a plurality of contacts and a plurality of traces, each of the plurality of contacts coupled with one or more of a plurality of electrodes via at least one of the plurality of traces.

18. A method, comprising:
providing a support comb of an implantable device, the support comb including:
   an attachment face to couple with an extension of a microelectrode film;
   a routing face having a slot; and
   a first finger and a second finger that define a channel, the channel to receive a wire;
coupling a first leg of a microelectrode film of the implantable device with the attachment face of the support comb;
positioning the wire through the slot of the routing face;
coupling the wire with the microelectrode film; and
forming a second leg of the microelectrode film about the support comb.

19. The method of claim 18, wherein the attachment face includes a channel, comprising:
disposing adhesive in the channel to couple the support comb with the microelectrode film.

20. A method, comprising:
providing a stimulation lead, the stimulation lead including:
   a microelectrode film, the microelectrode film including an extension;
   a support comb, the support comb including:
      an attachment face to couple with the extension of the microelectrode film;
      a slot to receive a wire; and
      a first finger and a second finger that define a channel, the channel to receive the wire.

* * * * *